United States Patent
Weinstein et al.

(10) Patent No.: US 6,270,466 B1
(45) Date of Patent: Aug. 7, 2001

(54) BRUXISM BIOFEEDBACK APPARATUS AND METHOD INCLUDING ACOUSTIC TRANSDUCER COUPLED CLOSELY TO USER'S HEAD BONES

(75) Inventors: Lee Weinstein, Arlington; Thomas E. Devlin, Somerville, both of MA (US); Karl T. Ulrich, Narberth, PA (US); Clay Burns, New York, NY (US)

(73) Assignee: BruxCare, L.L.C., Houston, TX (US)

( * ) Notice: Subject to any disclaimer, the term of this patent is extended or adjusted under 35 U.S.C. 154(b) by 0 days.

(21) Appl. No.: 09/341,720

(22) PCT Filed: Jan. 14, 1998

(86) PCT No.: PCT/US98/00692

§ 371 Date: Jul. 15, 1999

§ 102(e) Date: Jul. 15, 1999

(87) PCT Pub. No.: WO98/31277

PCT Pub. Date: Jul. 23, 1998

Related U.S. Application Data

(63) Continuation-in-part of application No. 09/194,237, filed as application No. PCT/US97/08641 on May 21, 1997
(60) Provisional application No. 60/035,536, filed on Jan. 16, 1997, and provisional application No. 60/018,316, filed on May 24, 1996.

(51) Int. Cl.[7] ......................................................... A61B 5/00
(52) U.S. Cl. ................................................................ 600/590
(58) Field of Search ................................. 600/546, 587, 600/590, 595

(56) References Cited

U.S. PATENT DOCUMENTS

| | | |
|---|---|---|
| 2,999,232 | 9/1961 | Wilson . |
| 3,978,847 | 9/1976 | Fehmi et al. ...................... 128/2.1 B |
| 4,934,378 | 6/1990 | Perry, Jr. . |
| 4,976,618 | 12/1990 | Anderson . |
| 4,995,404 | 2/1991 | Nemir ................................... 128/777 |
| 5,067,488 | 11/1991 | Fukada et al. . |
| 5,078,153 | 1/1992 | Nordlander et al. . |
| 5,190,051 | 3/1993 | Wilson . |
| 5,368,042 | 11/1994 | O'Neal et al. ......................... 128/733 |

OTHER PUBLICATIONS

Pierce and Gale, "A comparison of different treatments for nocturnal bruxism," *Journal of Dental Research*, 67 (3):597–601, Mar. 1988.

Hudzinski and Walters, "Use of a portable electromyogram integrator and biofeedback unit in the treatment of chronic nocturnal bruxism," *Journal of Prosthetic Dentistry*, 58 (6)698–701, Dec. 1987.

Burgar and Rugh, "Proposed standard measurement techniques for the technical specification of biofeedback devices," *Behavior Research Methods & Instrumentation*, 10 (5):632–638, 1978.

*Primary Examiner*—Max Hindenburg
(74) *Attorney, Agent, or Firm*—Steven J. Weissburg

(57) ABSTRACT

A method and apparatus for the treatment of bruxism thorough biofeedback is disclosed. In one embodiment, the apparatus consists of electronics mounted in a light-weight headband which may be worn comfortably by a user during sleep or while awake. Electrodes within the headband pick up surface EMG voltage signals indicative of bruxism, and bio-feedback is provided to the user by a piezoelectric transducer in mechanical contact with the head of the user. One electrode of the piezoelectric transducer also serves as the reference sense electrode. The electrodes require no chemistry, allowing the apparatus to be worn for considerable periods without skin irritation. Information detailing the timing, quantity, and duration of bruxing events may be stored internally for later retrieval via display, computer interface, or voice synthesis interface. When EMG signals satisfy certain pre-determined time and amplitude conditions, an acoustical bio-feedback signal is generated. The bio-feedback signal may start small and build up until the cessation of bruxing, when it may be rapidly terminated, facilitating treatment without waking a sleeping user.

9 Claims, 25 Drawing Sheets

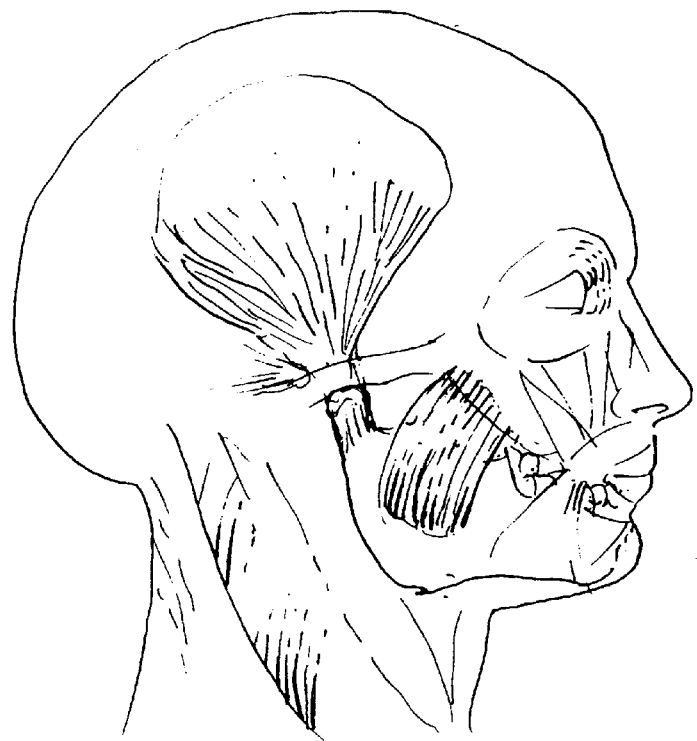
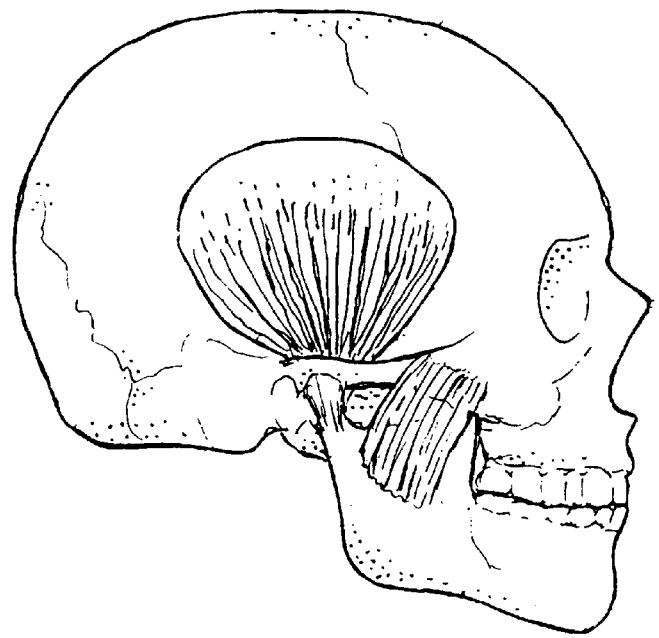
FIG. 1

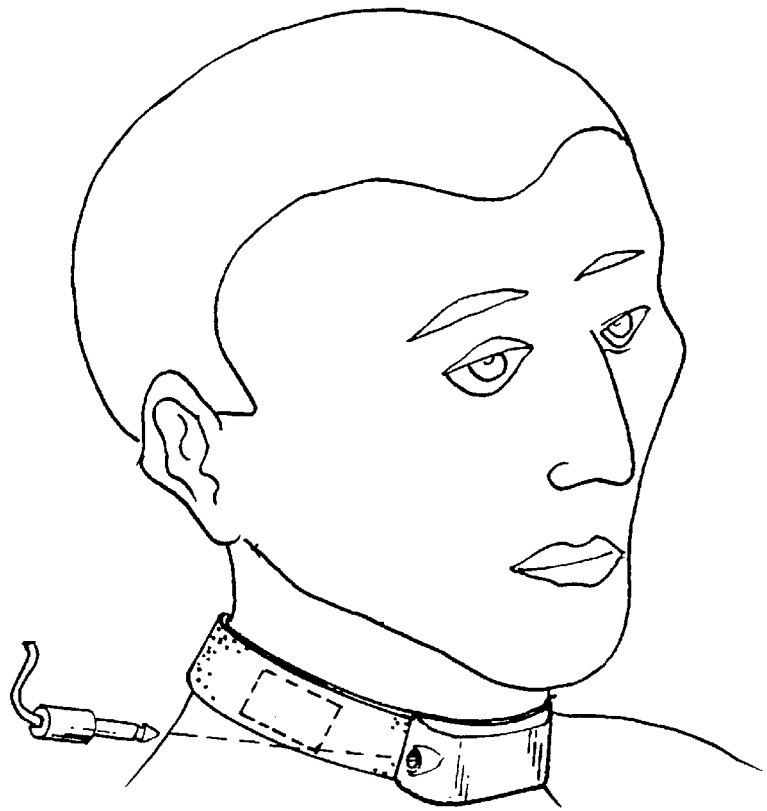
FIG. 4E
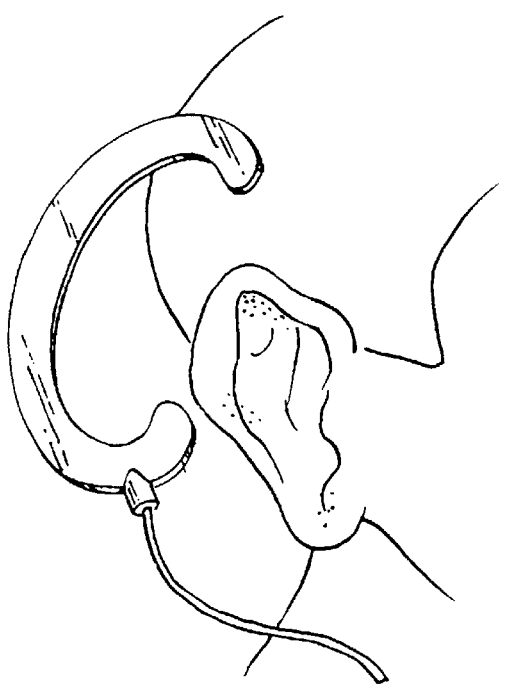 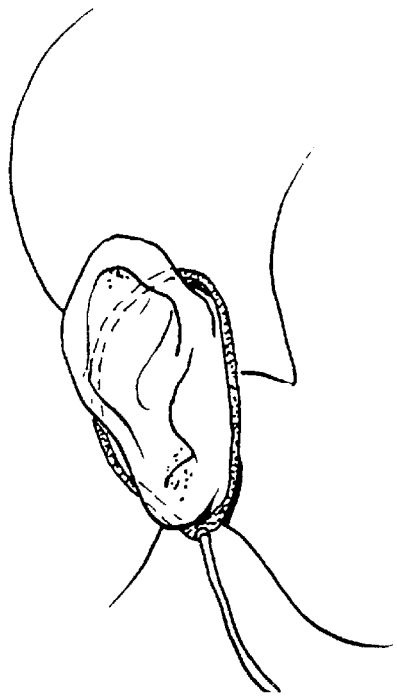
FIG. 4F        FIG. 4G

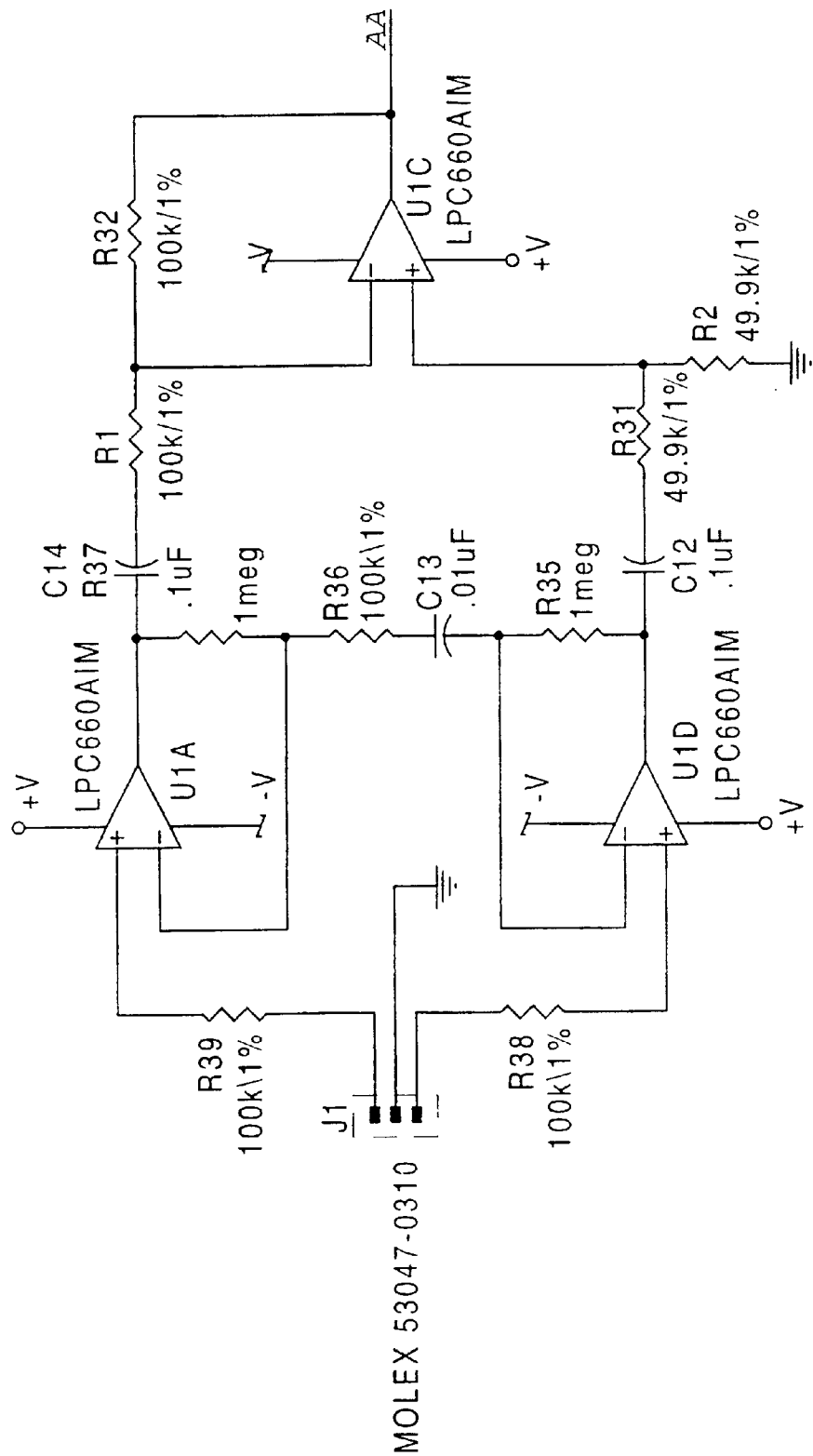
FIG. 7 Part 1
INSTRUMENTATION AMPLIFIER

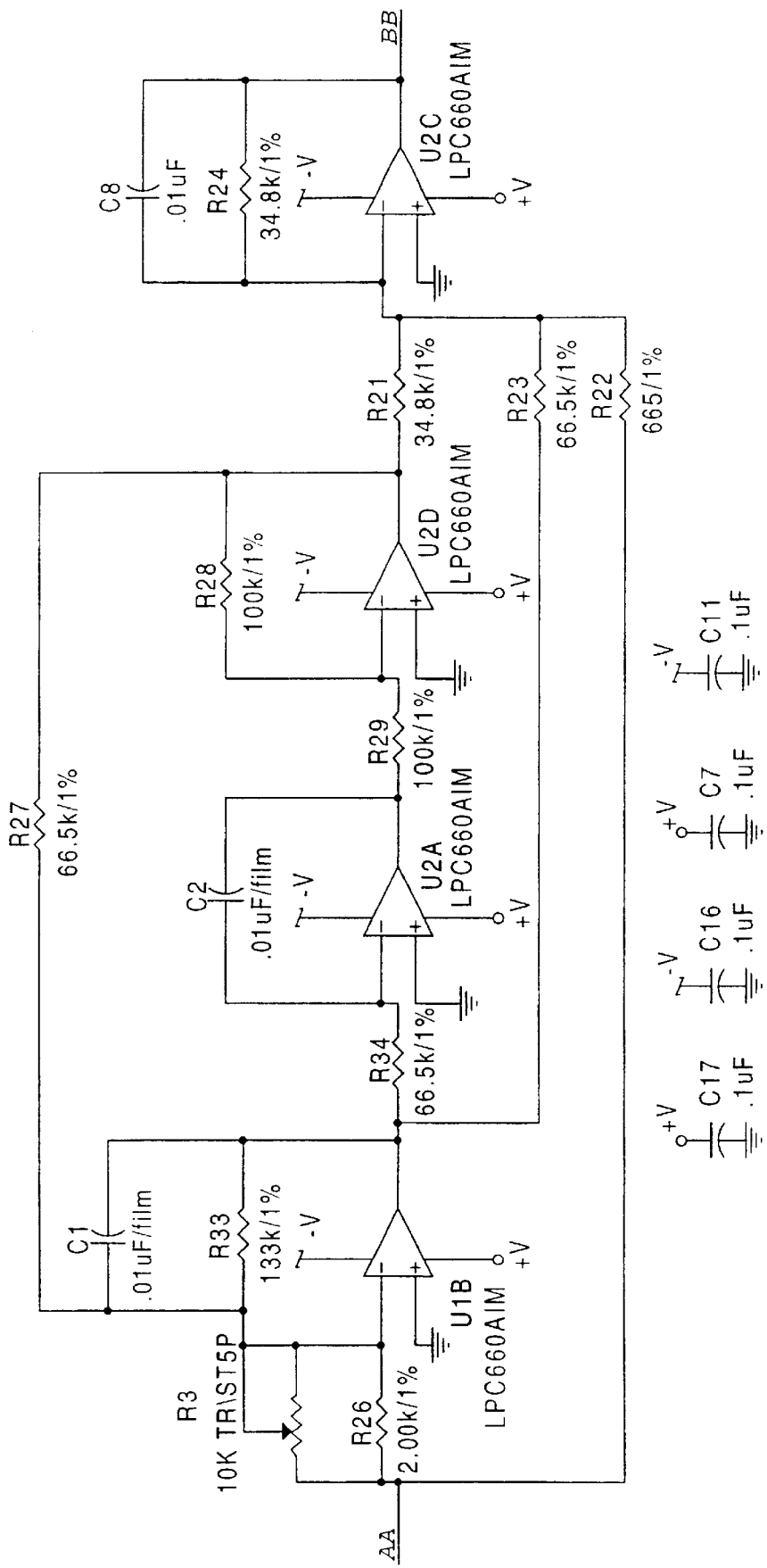
FIG. 7 Part 2
FILTER

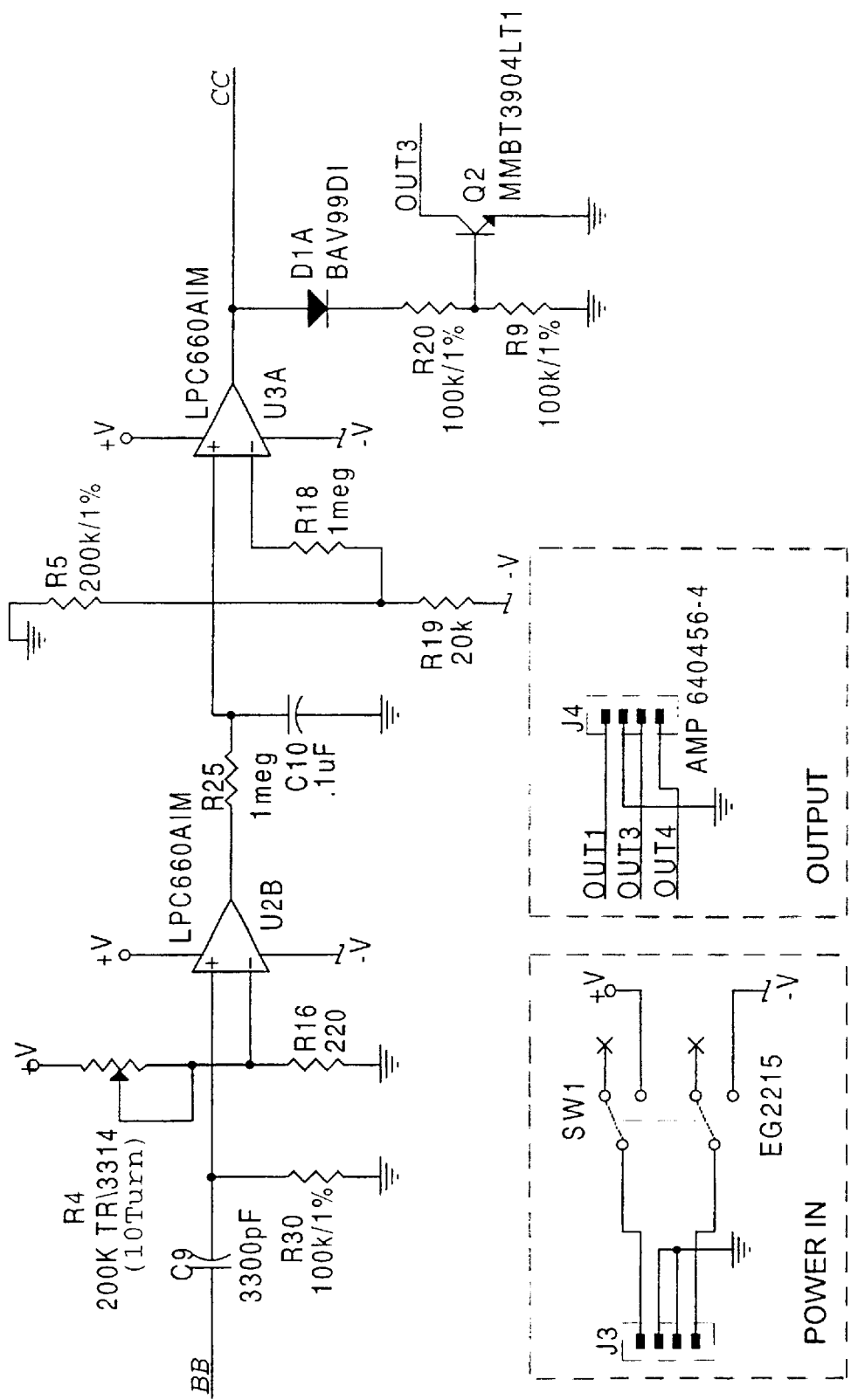
FIG. 7 Part 3

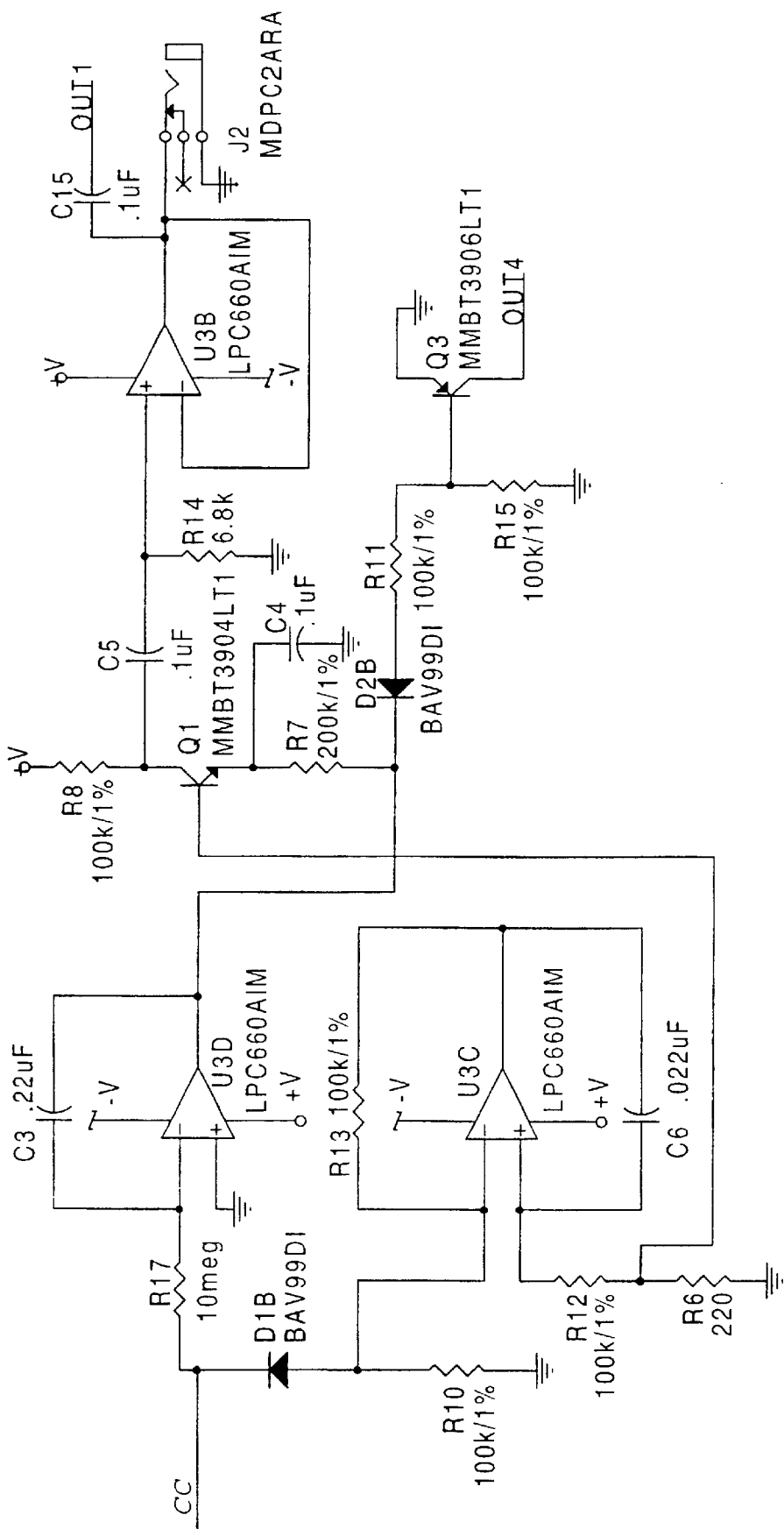
FIG. 7 Part A

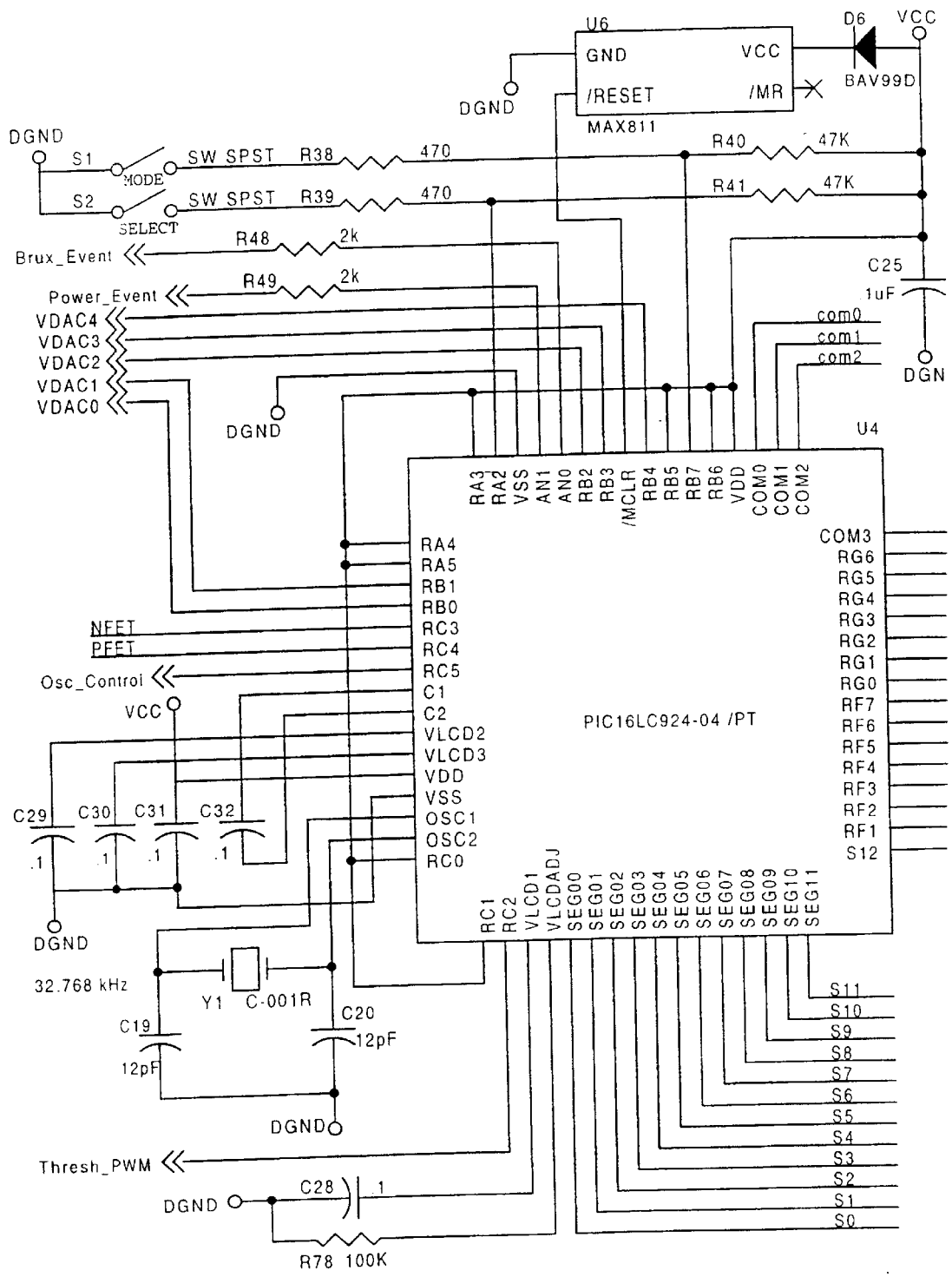
FIG. 9A Part 1

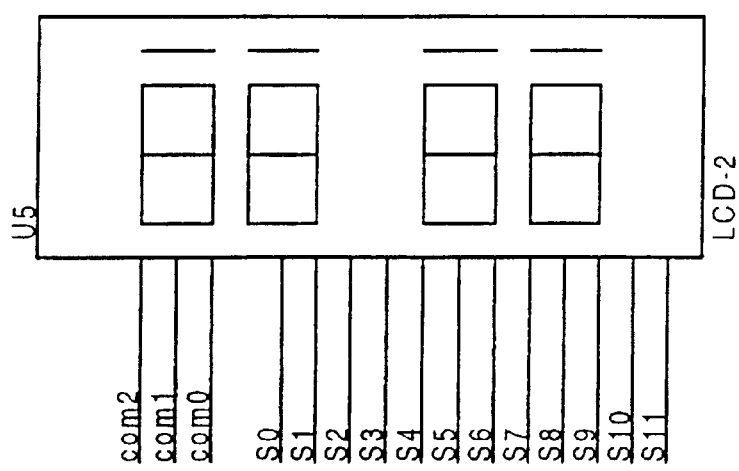
FIG. 9A Part 2

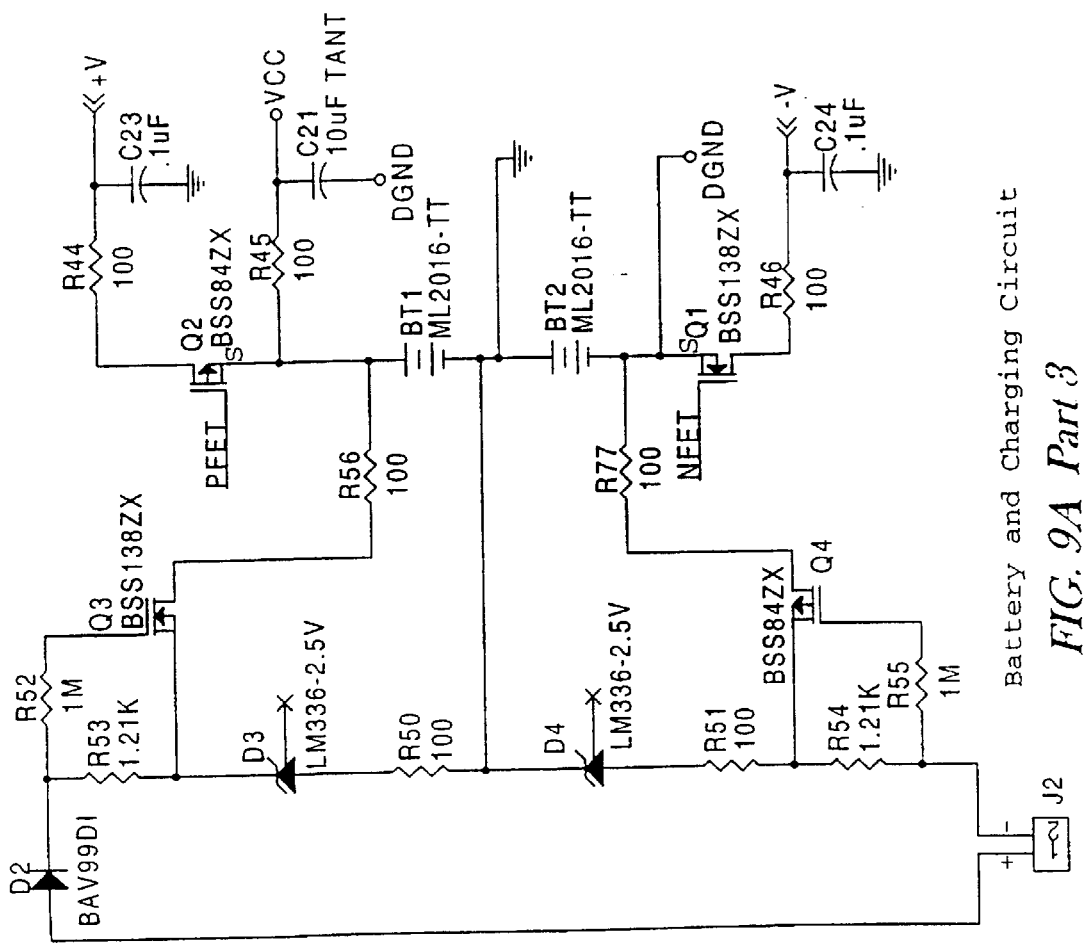
FIG. 9A Part 3

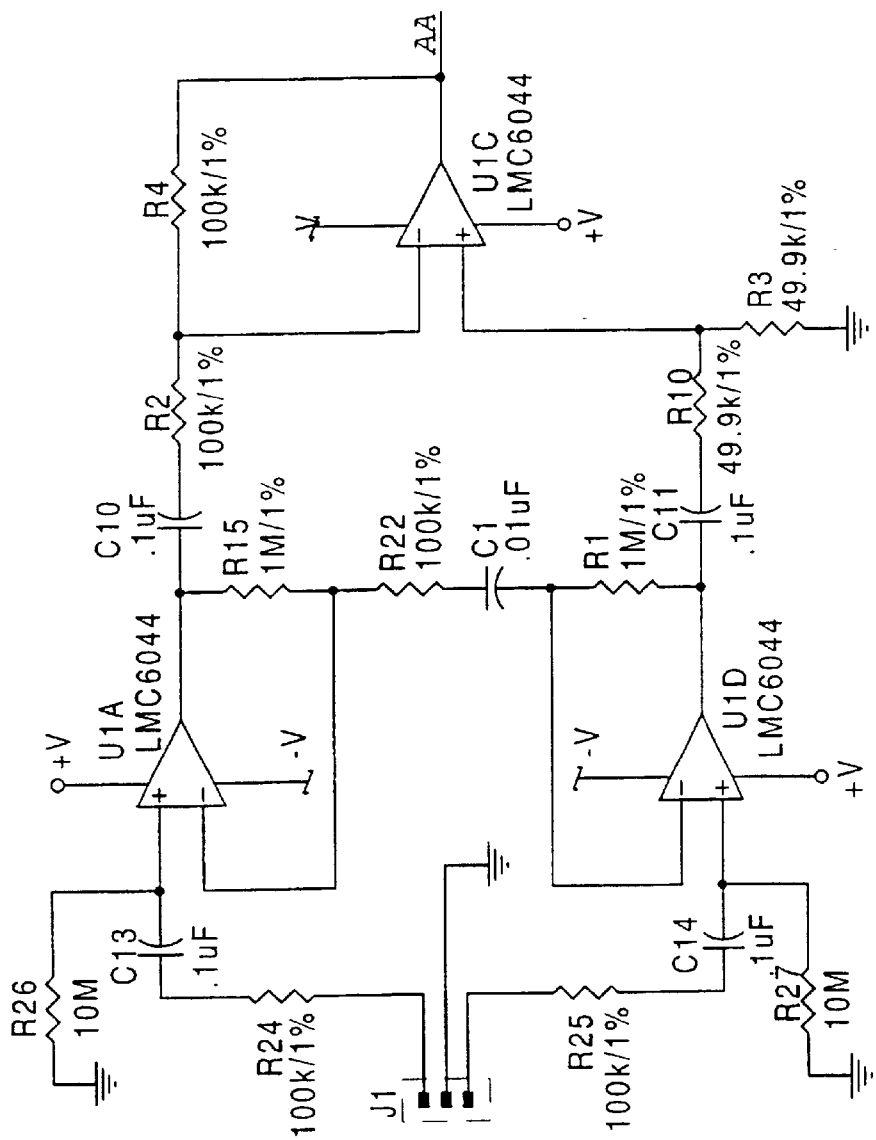
FIG. 9B Part 1

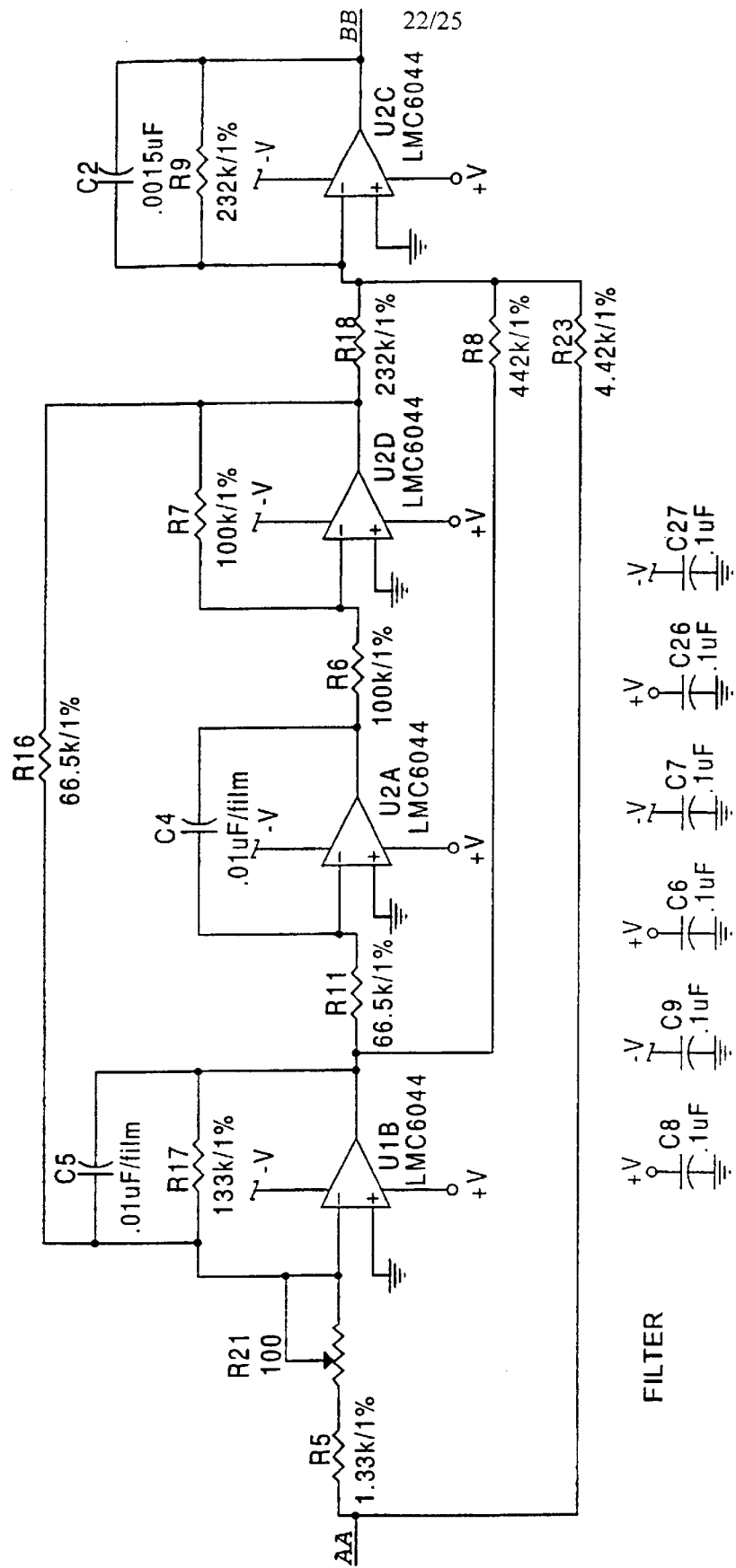
FIG. 9B Part 2

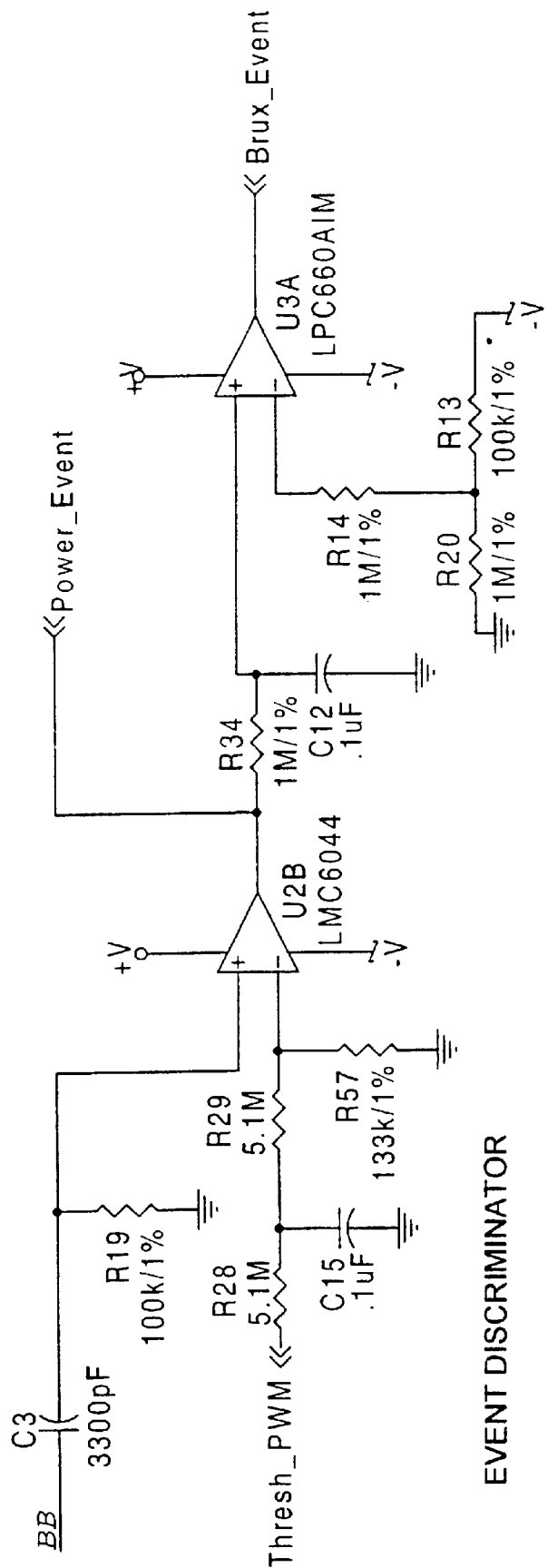
FIG. 9B Part 3

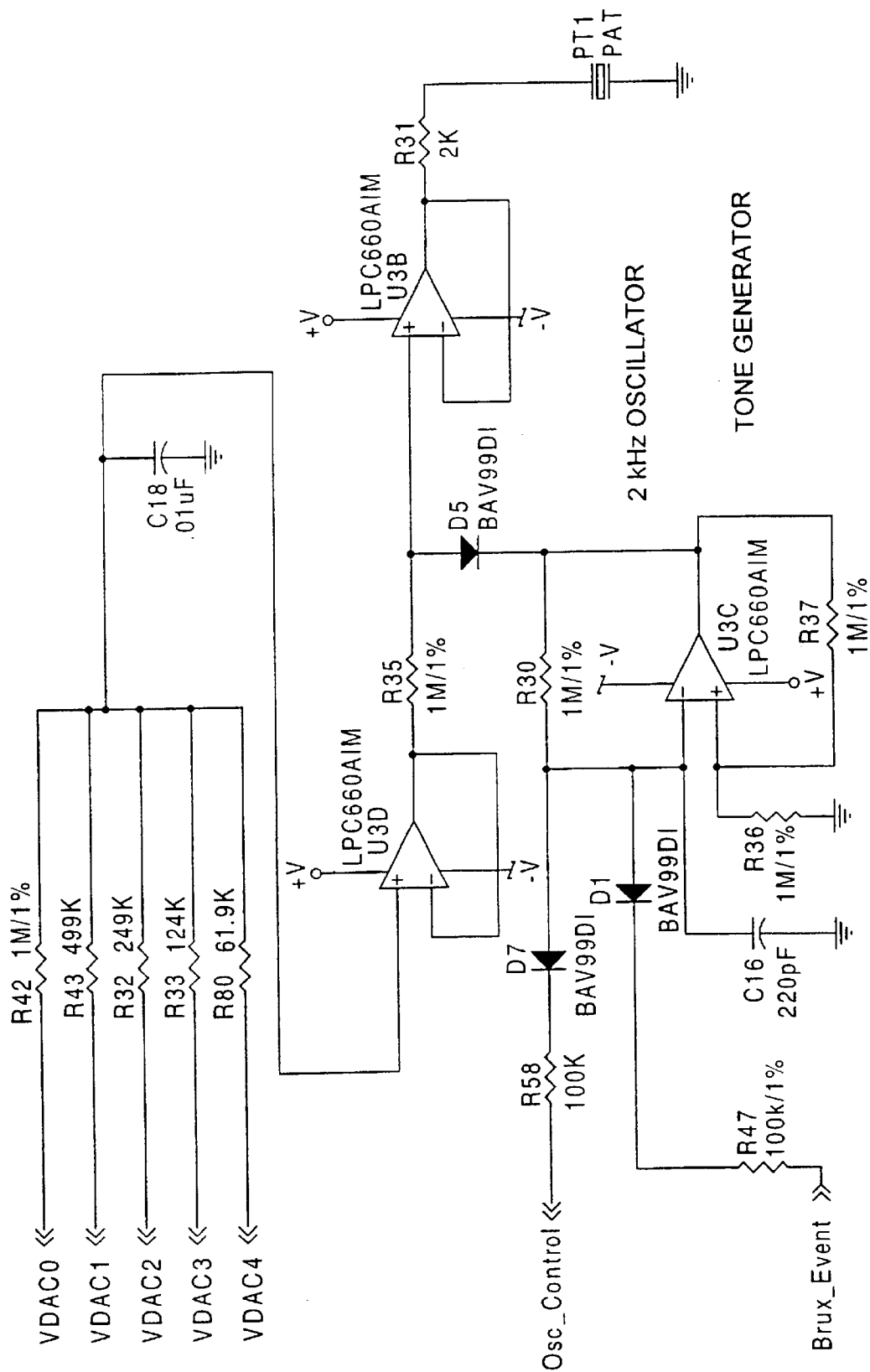
FIG. 9B Part 4

BRUXISM BIOFEEDBACK APPARATUS AND METHOD INCLUDING ACOUSTIC TRANSDUCER COUPLED CLOSELY TO USER'S HEAD BONES

This is the U.S. National Phase of application No. PCT/US98/00692, filed under the Patent Cooperation Treaty on Jan. 14, 1998, which claims priority from U.S. provisional application 60/035,536, filed Jan. 16, 1997. This also is a continuation-in-part of U.S. Ser. No. 09/194,237 filing date Nov. 23, 1998 now U.S. Pat. No. 6,117,092 which is the U.S. National Phase of application No. PCT/US97/08641, filed under the Patent Cooperation Treaty on May 21, 1997, which claims priority from U.S. provisional application 60/018,316, filed May 24, 1996.

BACKGROUND

The invention relates generally to the fields of electromyographic monitoring and biofeedback, and more specifically to biofeedback devices and techniques for treating bruxism.

Bruxism has generally been defined as the nonfunctional clenching, grinding, gritting, gnashing, and/or clicking of the teeth. Bruxism can occur while a person is awake or asleep. When the phenomenon occurs during sleep, it is called nocturnal bruxism. Even when it occurs during waking hours, the bruxer is often not conscious of the activity. Biting force exerted during bruxism often significantly exceeds peak biting force exerted during normal chewing. Biting forces exceeding 700 pounds have been measured during bruxing events. Chronic bruxism may result in musculoskeletal pain, headaches, and damage to the teeth and/or the temporomandibular joint.

The primary treatment for nocturnal bruxism is the use of intra-oral occlusal splints or "mouth guards," which are generally semi-rigid plastic covers for the upper or lower teeth. Occlusal splints are generally fabricated for a specific individual from an impression taken of the individual's teeth. While some studies have shown that the wearing of an occlusal splint may reduce bruxing event duration and intensity, the large replacement market for "chewed up" occlusal splints attests to the role of the splint primarily to protect teeth from damage, rather than as a cure for bruxism. Even as a symptomatic treatment, occlusal splints often only protect the teeth themselves, while the user may still suffer musculoskeletal pain and possible damage to the temporomandibular joint.

Occlusal splints present numerous inconveniences to the user. They require frequent cleaning, they are difficult to clean, they require periodic replacement, they inhibit speech, and they are frequently lost. For couples sleeping together, occlusal splints are far from "romantic." Some users perceive that occlusal splints accelerate tooth decay.

Dental researchers and clinicians have made several attempts to address the underlying causes of bruxism through biofeedback. Most commonly, an electromyograph was used to sense the action of the masseter muscle. When muscle activity was detected, an audible tone was generated. This tone alerted the individual that he or she was bruxing. The intention of this biofeedback approach was that a relatively short period of treatment would result in the long-term elimination of the bruxing behavior. Most of the shorter studies indicated that bruxism resumed once the treatment was discontinued. One longer study offered some evidence of sustained reduction in bruxism with longer term use and decreasing frequency of use of the biofeedback apparatus. Because these previous attempts to use biofeedback devices involved bulky electronics and required electrodes to be attached adhesively to the face, they were impractical for long-term use in treating bruxism, and not well suited for consumer use.

Some variations on this biofeedback approach known in the art incorporate sensing means into an occlusal splint in order to sense the onset of bruxing. These approaches require the presence of electrical devices in the mouth, including, in many cases, batteries, which may contain highly toxic substances. The electrical and chemical health risks of these devices add to the general drawbacks of intra-oral splints described above. In addition, many of these attempts have resulted in bulky devices which would be even more uncomfortable for the user than traditional occlusal splints.

It is the object of this invention to provide a convenient, comfortable, reliable, effective, economical, aesthetically pleasing means of providing long-term biofeedback to treat bruxism. It is a further objective of this invention to provide a bruxism treatment means which does not interfere with normal daily activities. It is a further object of this invention to avoid the presence of occlusal splints or other foreign objects in the mouth of the user. It is a further object of the invention to avoid the adhesive attachment of electrodes to the skin of the user. It is a further object of this invention to provide a user-friendly means for clinicians and bruxers to gather comprehensive data on the occurrence of bruxing events including time, duration, and intensity data. It is a further objective of this invention to provide a means for treatment of bruxism (or gathering of data on bruxism) which is wearable as an attractive, unobtrusive, comfortable article of clothing, which does not interfere with normal activities. It is a further object of this invention to provide a reliable, robust bio-feedback mechanism which is readily perceived by the user while remaining relatively unnoticable to persons in the user's immediate surroundings.

SUMMARY OF THE INVENTION

The general approach of the invention is to sense bruxing by sensing the electrical activity of "obruxism muscles" (the temporalis and/or masseter muscles used to close the jaw). The electrical signal from the bruxism muscles is processed by an electronics module. When a threshold of intensity and duration is exceeded, a signal is generated to provide feedback to the user, indicating the onset of a bruxing event. Data (including time, duration, and intensity) may also be stored internally in response to a bruxing event. These data may be read out through connection to a personal computer, or via voice synthesis or a display.

In one embodiment of the invention, three sensing electrodes are mounted to the inside of a headband which is worn around the user's head above the ears. One of these electrodes (the sense reference electrode) contacts the user near the center of the forehead and provides a reference bias voltage to assure that the input voltage at the sense electrodes is within the linear measurement range of the input amplifiers. The presence of a third electrode also allows for maximum input impedance on the other two electrodes (the sense electrodes). The sense electrodes are mounted such that they contact the user's head near the temples. The voltage between the temple electrodes is amplified and filtered to yield a signal indicative of the tension in the fibers of the temporalis muscle. In another embodiment sensing primarily the temporalis muscle (shown in FIGS. 2 and 3), the electrodes are implemented as the ear wires of a pair of eyeglasses (FIG. 4H). An alternate implementation for sensing primarily the temporalis muscle is an around-the-ear clip or conductive rubber band as shown in FIGS. 4F and 4G.

The electrodes are held in contact with the skin by spring or elastic force, requiring no adhesives. The electrodes are preferably made from materials which are impermeable to water. Moisture naturally present in the user's skin builds up between the electrode and the user's skin in a short time, allowing the skin to become conductive enough for the device to work without the need for special chemicals to be applied to the electrodes. The "moisture build-up" time is usually between 20 seconds and 2 minutes, and can be reduced essentially to zero if the user's skin is wiped with something damp just before putting on the apparatus.

Two embodiments sensing primarily the masseter muscle signal are shown in FIGS. 4A–4H.

In one embodiment the electronics module amplifies the voltage between the temporal electrodes in the frequency range 200 to 600 Hz (the frequency range in which the temporalis muscle is most active), while attenuating 60 Hz to enhance immunity to interference from magnetic and electric fields generated by common household wiring and appliances. A preferred embodiment uses a 60 Hz notch filter with a Q greater than 10. When the sensed voltage exceeds certain time and amplitude criteria, the electronics module generates an alert signal. The alert signal is an audible tone in a piezoelectric transducer worn by the user, and the volume of the tone increases until the sensed bruxing ceases, or until a maximum volume is reached. If the piezoelectric transducer is worn in contact with the user's head, such as at PET1, shown in FIG. 10 (and FIGS. 8A, 8C, 11, and 12), sound may efficiently be coupled to the user's skull so that it may be heard well in both ears at a level substantially louder than would be heard through the air by anyone near the user. This reduces the likelihood of disturbing a sleeping partner. Sound coupled through the air to others nearby may be further reduced by surrounding the side of the piezo electric transducer not in contact with the user with sound-absorbing material.

In order to reduce the potential interference with the sense electronics from signals coupled into the user by the piezo electric transducer, the electrode of the piezo electric transducer closest to the user's skin may be at ground potential (the reference potential for the input electrodes). If this electrode is allowed to contact the user's skin, it may actually serve as the reference sense electrode.

In addition to the audio tone, electrical signals indicative of threshold triggers and the instantaneous level of muscle electrical activity may be available as outputs for data recording for diagnostic purposes. These outputs may be connected to data recording apparatus either directly via wires, or via wireless transmission, such as infrared, radio frequency, or ultrasonic.

In a preferred head-band-style embodiment of the invention shown in FIGS. 8A, 8B, and 8C, the circuitry is assembled on a flex-circuit substrate 100 shown in phantom in FIG. 11. Regions of the substrate are stiffened to allow mounting of some components. A liquid crystal display (LCD) 102 and two user-actuatable buttons 104 and 106 on the front of the headband 50 allow the setting of various parameters such as sensitivity and alarm loudness, and the readout of event count and accumulated event duration information. Rechargeable batteries 108 (FIG. 12) allow the unit to operate for over a week under normal usage patterns (8 hours per day). Batteries 108 are recharged by attaching two clips to two externally exposed rivets 110 (FIGS. 8C and 12). The circuitry is sewn inside a flexible rubberized fabric 112 (FIG. 8B), which increases comfort, gives aesthetic appeal, and affords protection of sensitive circuit components from external static discharge. Fabric-reinforced conductive rubber electrodes are riveted 114 to the flex-circuit through the rubber/fabric enclosure, which is folded over 116, and sewn to itself). This allows a gas-tight electrical connection from the flex-circuit to the electrode (offering long-term reliability and resistance to corrosion). This electrode attachment also aesthetically covers the connection rivets 114, and keeps them out of contact with skin chemistry, reducing corrosion and discomfort. Piezoelectric transducer PET1 provides an acoustical bio-feedback signal to the user, indicative of bruxing activity. One electrode of Piezoelectric Transducer PET1 contacts the user's skin and serves as the reference input electrode.

BRIEF DESCRIPTION OF THE FIGURES

FIG. 1 shows schematically, a muscle diagram, showing the location of the temporalis and masseter muscles (the muscles used for chewing).

FIG. 4E shows an embodiment where the electrodes are held in contact with the user's skin just below the jaw via an elastic: neck band.

FIGS. 4F and G show alternate preferred embodiments of the invention for around the ear electrode schemes for sensing the masseter muscle.

FIG. 7 Part 1 shows an instrumentation amplifier portion of a circuit schematic of a preferred embodiment of the invention.

FIG. 7 Part 2 shows a filter portion of a circuit schematic of the embodiment of the invention shown in FIG. 7 Part 1.

FIG. 7 Part 3 shows the power in and output portion and other portions of a circuit schematic of the embodiment of the invention shown in FIG. 7 Part 1 and FIG. 7 Part 2.

FIG. 7 Part 4 shows additional portions of a circuit schematic of the embodiment of the invention shown in FIG. 7 Part 1, FIG. 7 Part 2 and FIG. 7 Part 3.

"FIGS. 9A and 9B: Detailed circuit diagram of a preferred embodiment of the invention, where a microprocessor, digital display, and two switches allow setting of sensitivity, alarm volume, and on/off functions, and where cumulative data on number of bruxing or clenching events and total duration of bruxing and clenching can be displayed. In this embodiment, the microprocessor automatically shuts off power to the analog circuitry and goes into a super-low power sleep state after seeing an above-trigger-level signal for more than 30 seconds," and insert therefor:

FIG. 9A Part 1 shows a microprocessor portion of a detailed circuit diagram of a preferred embodiment of the invention.

FIG. 9A Part 2 shows a digital display portion of a detailed circuit diagram of the embodiment of the invention shown in FIG. 9A Part 1.

FIG. 9A Part 3 shows a battery and charging circuit portion of a detailed circuit diagram of the embodiment of the invention shown in FIG. 9A Part 1 and FIG. 9A Part 2.

FIG. 9B Part 1 shows an instrumentation amplifier portion of a detailed circuit diagram of a preferred embodiment of the invention.

FIG. 9B Part 2 shows a filter portion of a detailed circuit diagram of the embodiment of the invention shown in FIG. 9B Part 1.

FIG. 9B Part 3 shows an event discriminator portion of a detailed circuit diagram of the embodiment of the invention shown in FIG. 9B Part 1 and FIG. 9B Part 2.

FIG. 9B Part 4 shows a tone generator portion of a detailed circuit diagram of the embodiment of the invention shown if FIG. 9B Part 1, FIG. 9B Part 2 and FIG. 9B Part 3.

DETAILED DESCRIPTION

Figure 6A:
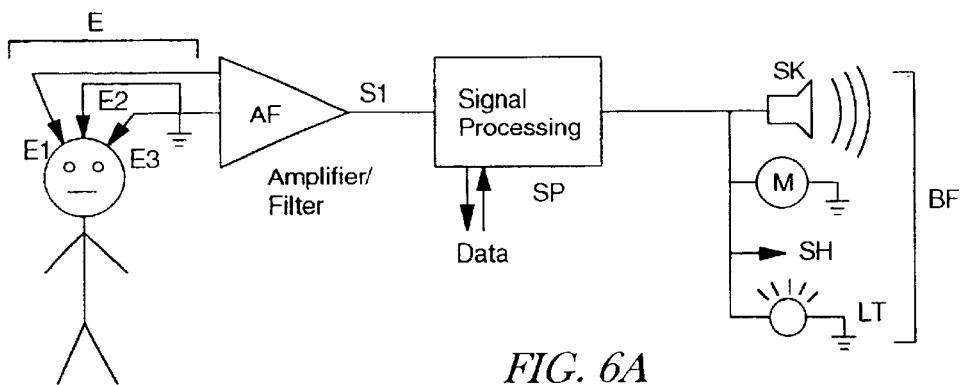
FIGS. 6A–6C shows circuit block diagrams of alternative embodiments of the invention.

A generalized block diagram of the invention is shown in FIG. 6A. A set of electrodes E held mechanically in contact with the user's skin picks up signals generated by bruxism muscles (along with electrical noise and interference). Differential signals from at least one pair of electrodes are selectively amplified by Amplifier/Filter AF. The output of amplifier/filter AF is a signal S1, indicative of the activity level of bruxism muscles. Signal S1 is processed by signal processing means SP to determine when the bruxing activity present is worthy of some action (such as recording as data, or providing biofeedback). The intent of providing biofeedback is to provide the user with a perceivable signal, which, when present, will cause the instinctive or automatic interruption of the bruxing activity. Biofeedback means BF may be implemented as audio feedback means SK (such as a piezoelectric transducer or earphone), vibratory feedback means M, electrical shock feedback means SH, or light feedback means LT.

Figure 2:
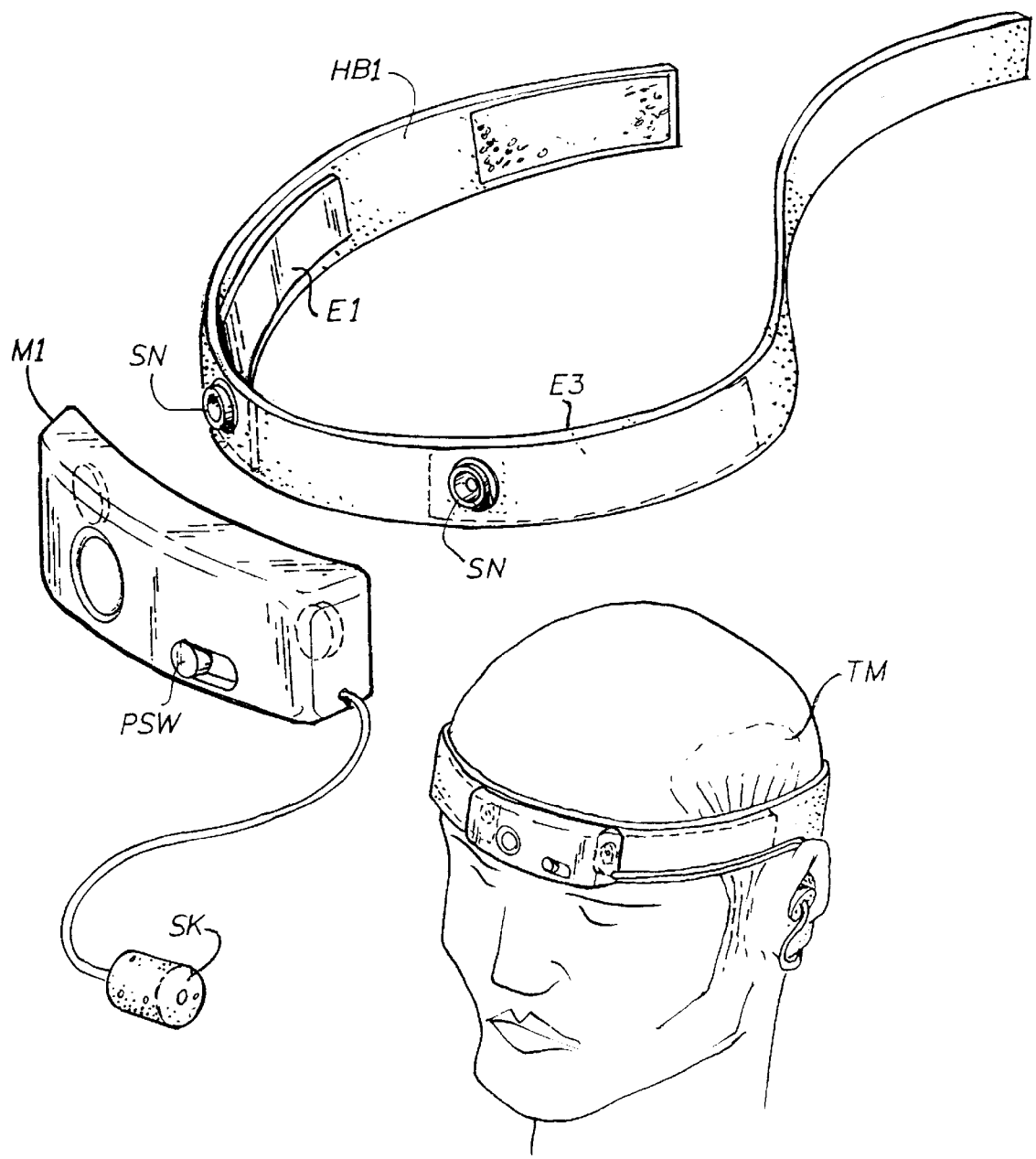
FIG. 2 is a schematic view of a headband of the invention on a user's head, showing how electrodes of an embodiment of the invention are located relative to the temporalis muscles.

FIG. 2 is a perspective view of a two-electrode implementation. Conductive rubber sense electrodes E1 and E3 are sewn inside headband HB1. Electrodes E1 and E3 contact the user's head near the temples, and pick up signals from the temporalis muscles TM. Electrodes E1 and E3 are connected via snaps SN to electronics module M1. In-the-ear audio bio-feedback transducer SK is hard-wired to electronics module M1. Slide witch PSW turns on and off power to electronics module M1.

Figure 3:
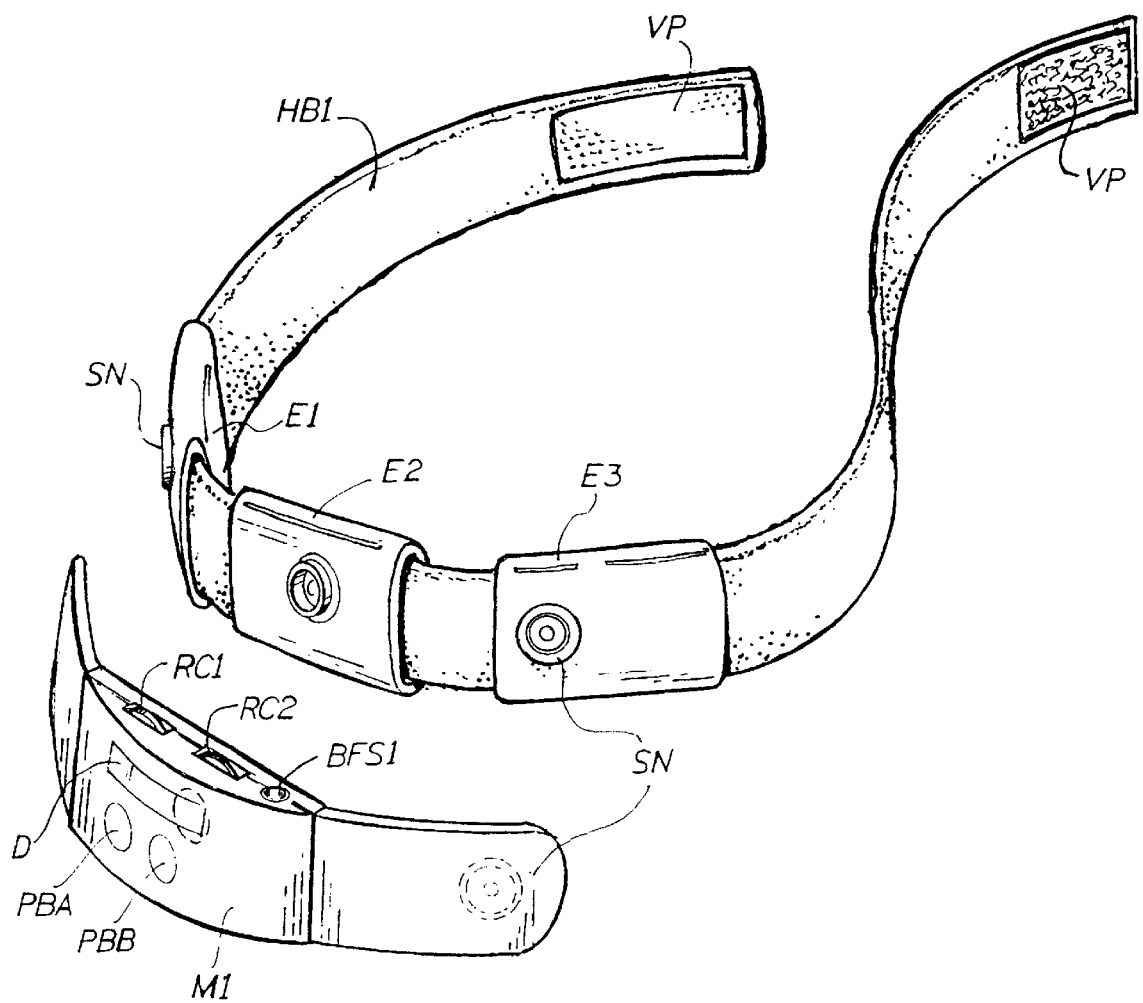
FIG. 3 is a partially exploded view of a headband mbodiment of the invention, showing the electrodes and an electronics module.
Figure 4A:
FIG. 4A shows an embodiment where the electrodes are implemented as conductive ear-contacting pads on a headphone-type "C" shaped head band.
Figure 4B:
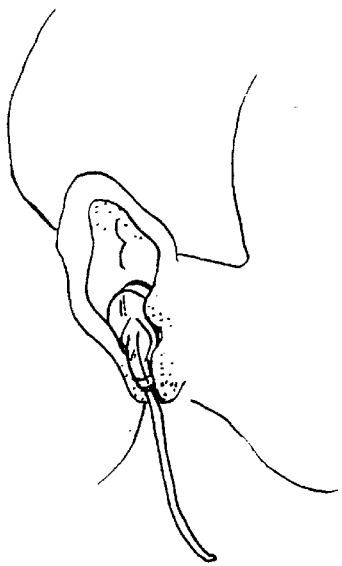
FIG. 4B shows an embodiment where the electrodes are implemented as a pair of conductive, in-the-ear plugs.
Figure 4C:
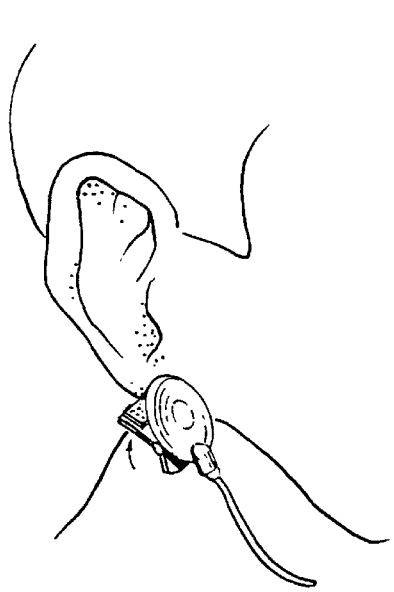
FIGS. 4C and 4D show an embodiment where the electrodes are implemented as a pair of clip-on or through-the-ear earrings respectively.
Figure 4D:
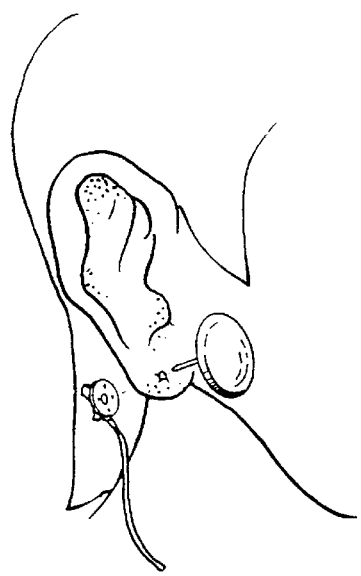
Figure 4H:
FIG. 4H shows an embodiment of the invention including electrodes as glasses frames, for sensing the signal on the temporalis muscles.

FIG. 3 is a perspective view of an embodiment where the electronics are contained within snap-on module M1. Snap-on odule M1 connects to sense electrodes E1 and E3 (which contact the sides of the head near the temples) via snaps SN. Ground reference electrode E2 contacts the forehead. Headband HB1 is free to slide back and forth through loop-shaped electrodes E1, E2, and E3, allowing the headband to shift some without moving the electrodes. Headband HB1 is fastened via hook and loop type fastener patches VP. Operational characteristics (such as audio bio-feedback volume, trigger sensitivity, and reading out and clearing stored data) are controlled by push-button switches PBA and PBB. Stored data such as number of events and total seconds of bruxing activity may be read out on display D. In some embodiments, bio-feedback volume and trigger sensitivity may be controlled by rotary analog controls RC1 and RC2. Audio biofeedback may be provided through a piezoelectric element of an earphone connected to socket BFS1. Recharging of internal rechargeable batteries may also be accomplished through socket BFS1.

Figure 10:
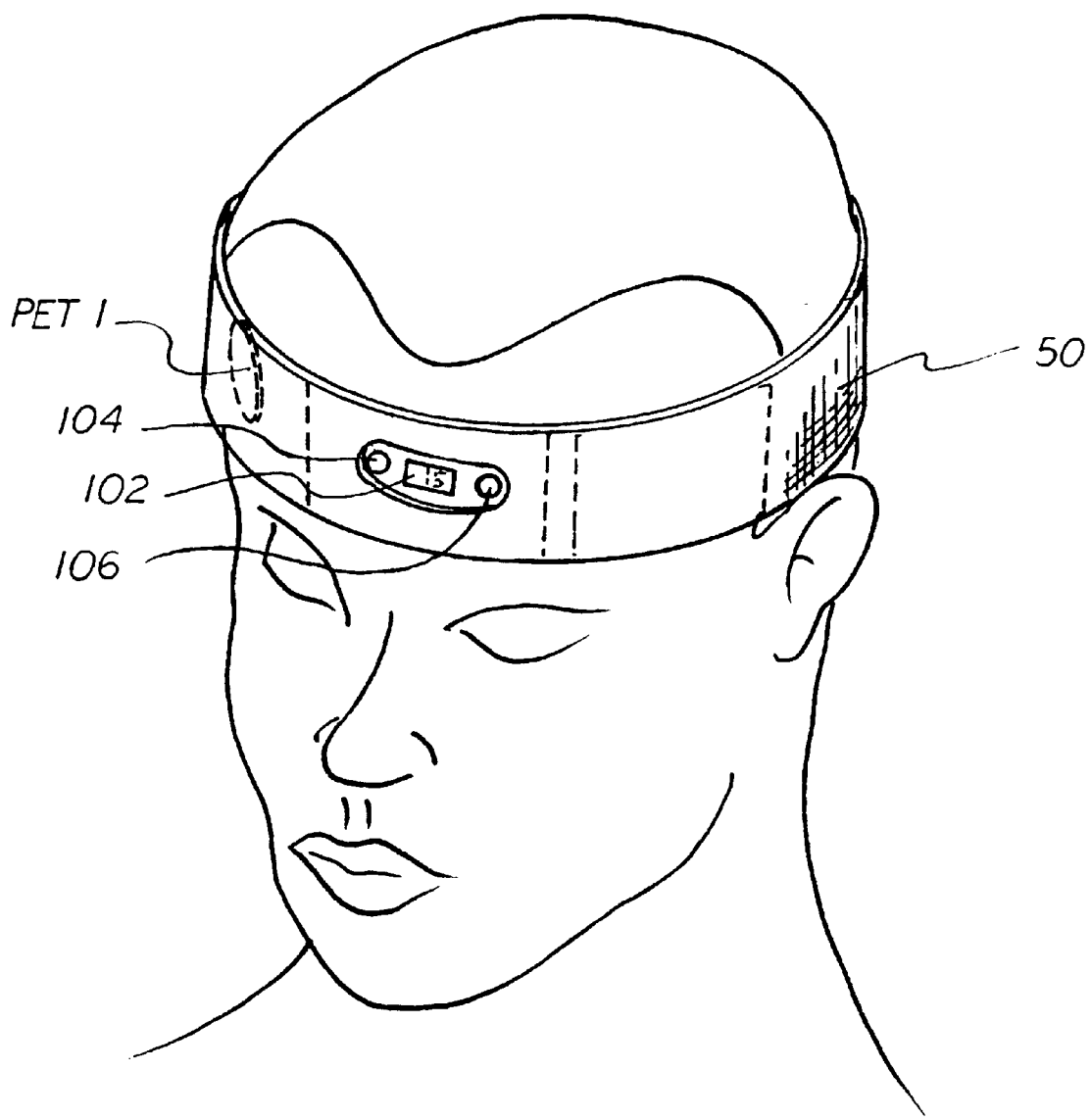
FIG. 10 is a schematic view (with some hidden parts shown) of a preferred headband-type embodiment of the invention, on the head of a user.

In the embodiment shown in FIGS. 8A, 8C, 10, 11 and 12, a piezo electric transducer PET 1 is used to provide audio feedback to the user. The piezo electric transducer PET 1 is mounted in the headband as shown, such that its metal (e.g. stainless steel) cover 118 (FIG. 12) is in direct contact with the skin of the user's forehead, as shown in FIG. 10. This cover, 118, may also serve as the reference (ground) input electrode E2 for the input circuit. This arrangement provides a significant degree of acoustic coupling to the bones of the user's head, and thus to the user's auditory system, without providing any significant coupling to the air around the user. Further, acoustic transmission to the air can be further damped by surrounding the surfaces of the piezo electric transducer that face the air with an acoustic damper. A suitable piezo electric transducer is one of the type that is commonly used in a low cost digital alarm watch.

Figure 8A:
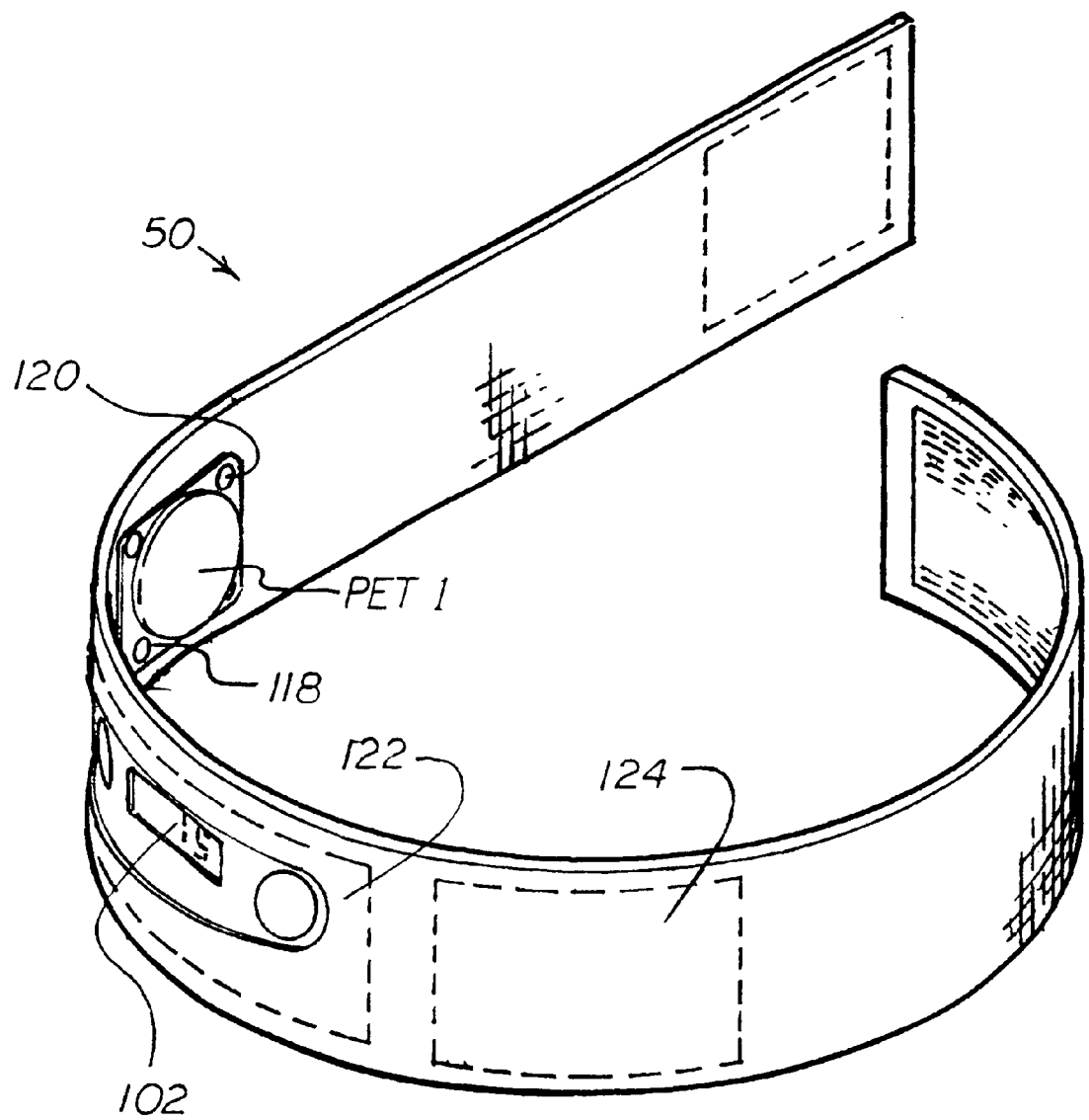
FIG. 8A is a schematic view, predominantly from the side that faces away from a user, showing electrodes and an electronics module.
Figure 11:
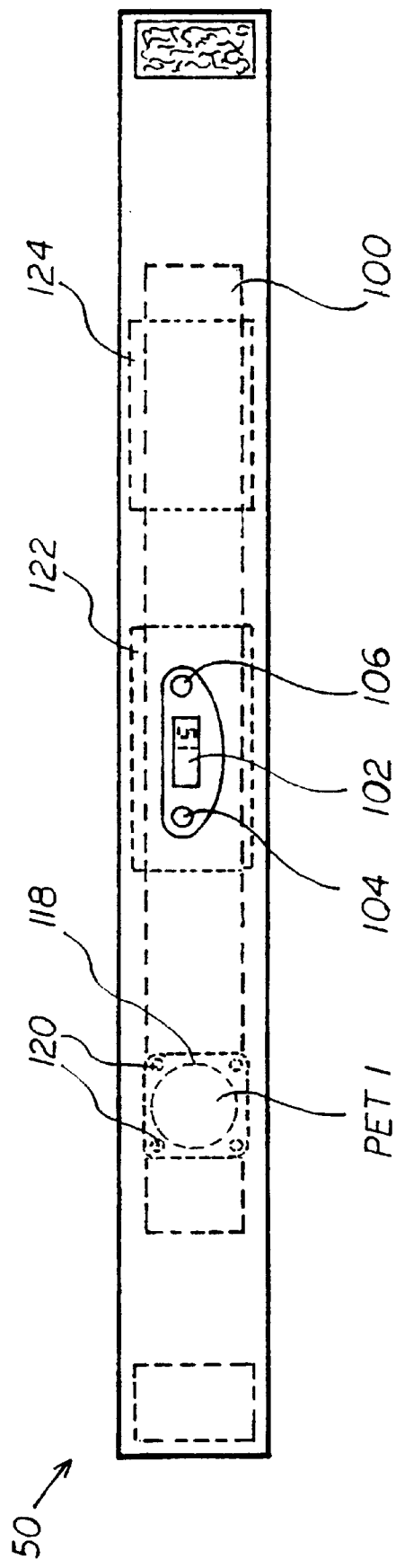
FIG. 11 is a schematic view (with some hidden parts shown) of a preferred headband-type embodiment of the invention, unclasped.
Figure 12:
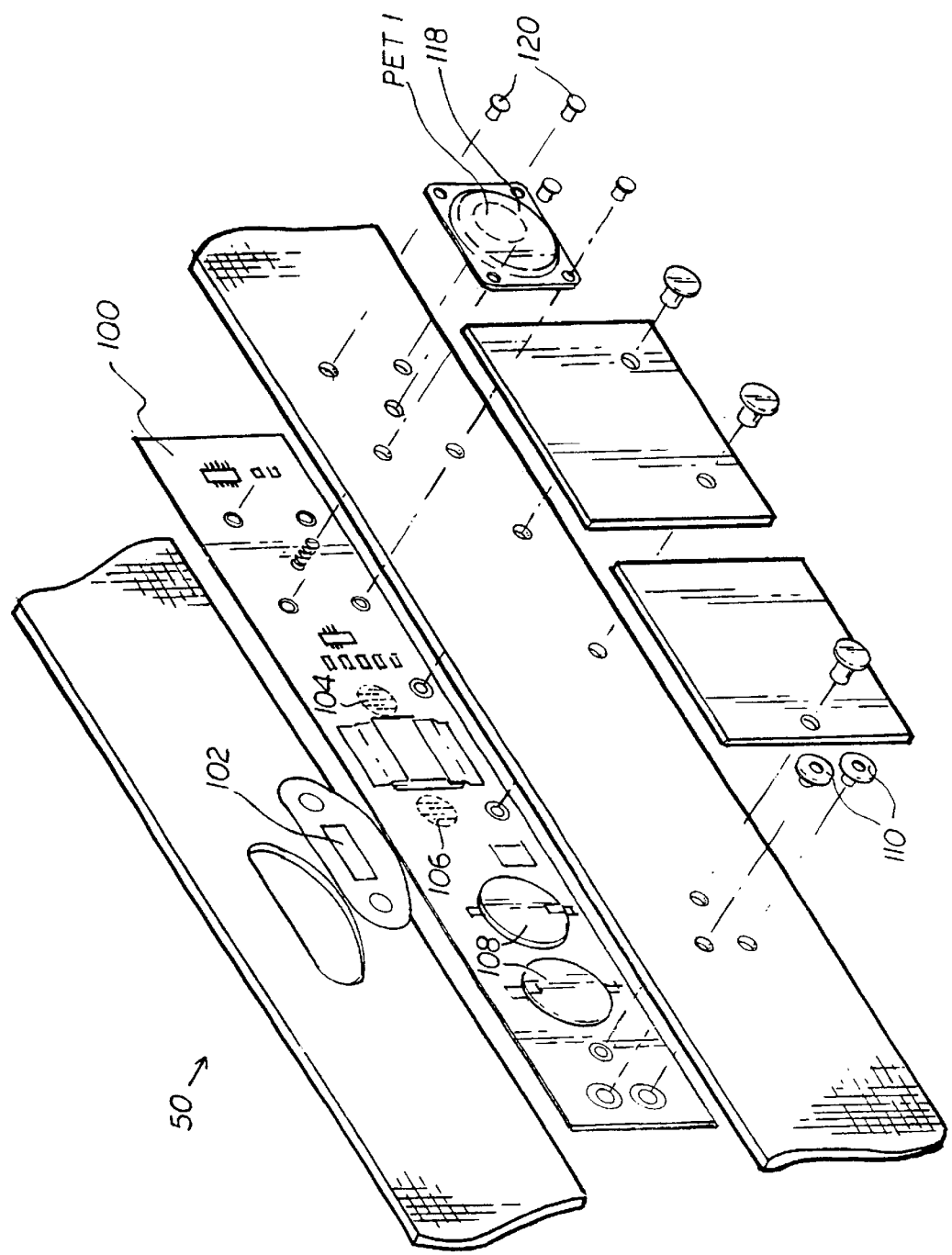
FIG. 12 is an exploded schematic view of a preferred headband-type embodiment of the invention.

As shown in FIGS. 8A, 11, and 12, rivets 120 can connect the piezo electric cover to the flexible circuit substrate 100, so that it can serve as the electrode.

Figure 8B:
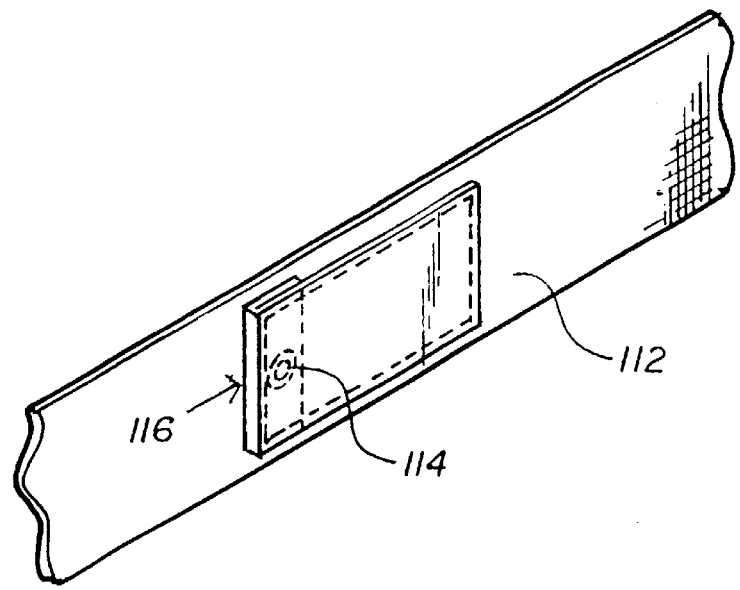
FIG. 8B is a schematic view from the side that faces the user showing how folded over fabric/rubber electrodes are electrically connected and mechanically sewn in place.
Figure 8C:
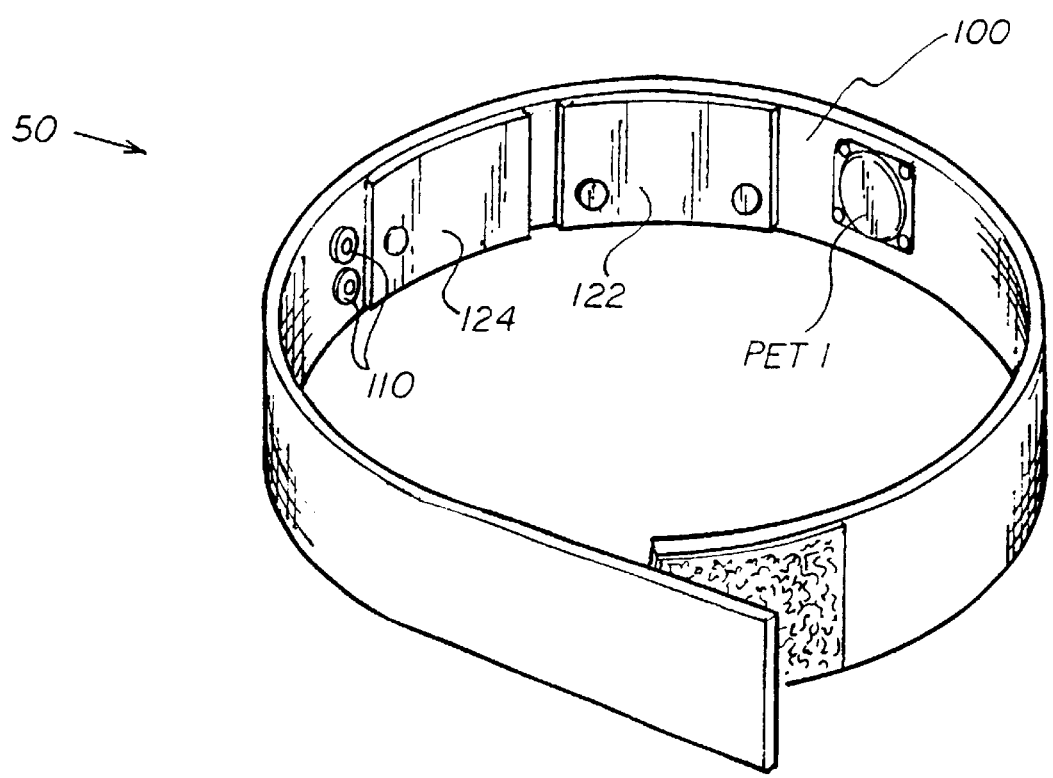
FIG. 8C is also a schematic view, predominantly from the side of a preferred embodiment that contacts the user, also showing the electrodes and an electronics module and showing how the stainless steel back of a piezoelectric transducer acts as ground reference electrode.

Each of the two electrodes 122 and 124, serving the functions of E1 and E3, respectively, discussed above, can be conductive rubber patches that are sewn to the inside (user-facing surface) of the headband. The patches are themselves electrically connected to the flexible circuit board, such as with rivets 114, shown in FIG. 8B. In this manner, the rubber electrodes are conductively connected to both the user's forehead and the circuitry. In the embodiment shown in FIGS. 8A, 8C, 11 and 12, the cover 118 serves as the third electrode, E2. It is also possible, instead, to use a conductive rubber patch similar to that shown at 122.

Normally, the function of the electrode set E and the amplifier/filter AF can be thought of as linear. Any increase in bruxing activity will cause a proportional increase in bruxism signal S1. It is often desirable that the processing after S1 be non-linear. For instance, it may be desirable that only events stronger than a certain threshold are ever logged as data or seen as sufficient to warrant biofeedback. The defining of this threshold is a non-linear operation. Anything less than the threshold results in no output, and anything above the threshold results in an output. The key variables of interest in processing bruxism signals are amplitude (or intensity) and time (duration, repetition rate, etc.). It may, for instance, be desirable to detect repetitive brief clenching of the jaw, as well as sustained clenching, while it may also be desirable not to detect a single, isolated, brief muscle contraction, such as might happen when the user shifts position in bed.

It is desirable for the input stage of amplifier/filter AF to be robust in several key ways. First, in connecting conductively to the skin of a person, the chemistry of the connection interface may vary widely. These chemical variations may come from sweat, lotions, perfume, etc. Differing surface chemistry at two different electrodes can result in a significant offset voltage. This voltage is like a small unknown battery creating a voltage in at the electrodes, and may be thousands of times the amplitude of the relevant signal. This offset voltage varies very slowly compared to the frequencies of interest in the bruxism signal, so it can be conveniently filtered out by high-pass filtering (also known as "AC coupling"). It is desirable that the break frequency of the high-pass filter is at or below 200 Hz, in order not to attenuate any of the relevant bruxism signal.

It is desirable that the input impedance of amplifier/filter AF be high, and that the needed bias current for the input stage be as low as is practical. A high input impedance and low bias current results in the lowest possible current flowing through the person's skin. This is desirable both from a regulatory standpoint (UL regulations in the USA, and other analogous regulations abroad), and from an electrochemical standpoint. Any current that flows completes a chemical reaction at the surface of the skin, and will, to some extent, combine the electrode material with that of the user's skin. This can cause staining of the skin, irritation, etc.

It is also desirable that the input stage be designed to withstand common static discharges, as those a person might experience after walking across a carpet and touching something conductive, or as might occur when playing with a pet cat. It is also desirable that the amplifier/filter have a negligible response to common forms of electromagnetic interference. The most relevant being 60 Hz interference as might be picked up from common household utility wiring and appliances.

Figure 6B:
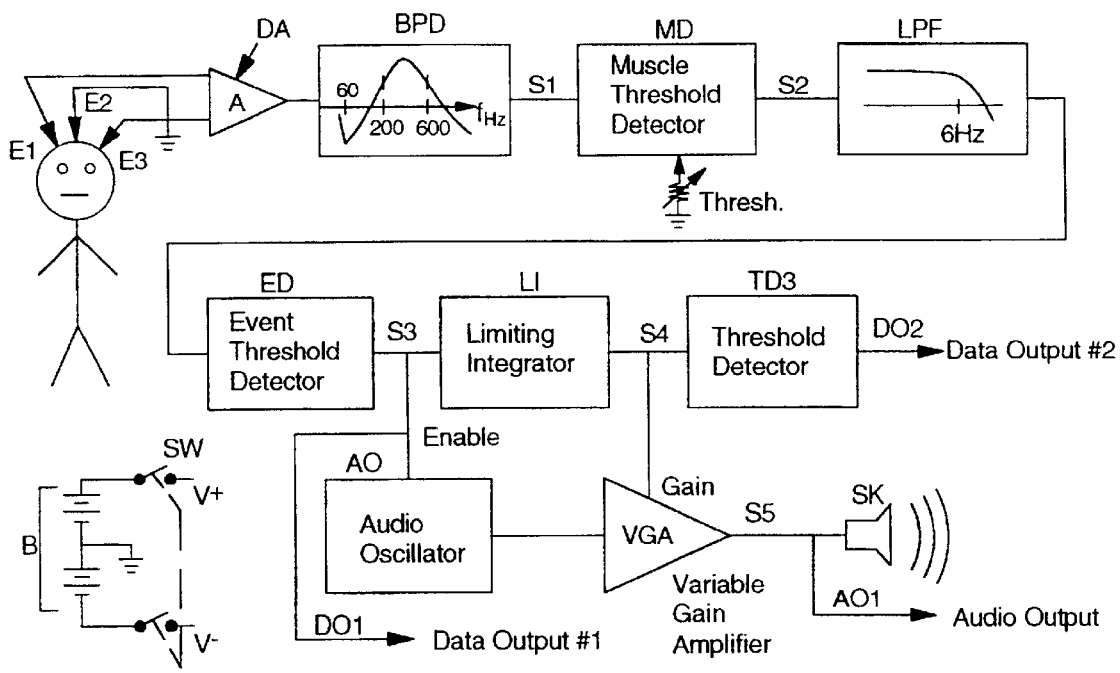
Figure 6C:
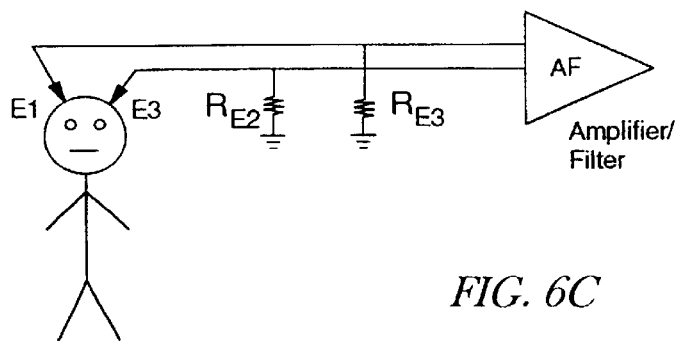

In order to sense the signal from the bruxigm muscles, at least two electrodes (E1 and E3) are required. If a third electrode is added, the input impedance of the amplifier/filter AP may be maximized. In order for any amplifier to operate, some (normally minute) bias current must be provided for its inputs. This bias current is needed to maintain the amplifiers inputs within their operational voltage range. The addition of a third electrode E2 allows this current to be supplied without compromising the input impedance of the amplifier. In FIGS. 6A and 6B, this third electrode E2 is shown connected to electrical ground. It is assumed here that electrical ground as it is defined in the circuitry is within the operating voltage range of the input amplifier. As an alternative to providing a third electrode as shown in FIG. 6C, resistors RE1 and RE3 may be provided to allow the biasing of the amplifier. The addition of RE3 and RE4 will, however, always result in a lower input impedance (and therefore a chemically more interactive set of electrodes). Another disadvantage of a lower input impedance is that a lower electrode contact resistance will be required for reliable detection of the signal from bruxing muscles. Thus a lower input impedance makes the design of reliable electrodes harder. For a system using no electrode chemistry to reduce skin resistance, it is doubly important to provide a high input impedance.

A more detailed block diagram of one embodiment of the invention is shown in FIG. 6B. Here amplifier/filter AF has been expanded into separate amplifier (DA) and filter (BPF) functions. Three electrodes E1, E2, and E3 are held in contact with the user's skin without the aid of adhesives. The signal sensing electrodes E1 and E3 are disposed on opposite sides of the user's head, and provide signal input for differential instrumentation amplifier DA. It is also possible to place one of the sense electrodes on the user's forehead, and for the ground electrode to be toward one side of the head, but this configuration provides less immunity to triggering by eyebrow movement and other use of facial muscles. Electrodes E1 and E3 pick up the desired muscle potential signal (along with undesired environmental electrical noise and interference) conductively through the skin. The reference electrode E2 contacts the user preferably somewhere near the median plane bisecting the head, and provides a ground reference and needed minute bias current for amplifier DA. The muscle signals of interest are typically in the range of 0.01 to 0.1 mV in amplitude. These signals are generated by electrochemical depolarization and repolarization within muscles and nerves as the individual muscle cells "fire" and contract. Throughout a muscle, individual muscle cells fire at different times in different places. This can be thought of as a process like popcorn popping. The overall strength of contraction of the muscle at a given moment comes from how much corn per second is popping at the time. If one looks at the overall electrical signal from a muscle, it can be thought of as the noise the popcorn makes. Unlike popcorn, however, the muscle cells don't fire only once, they fire and then relax and then can fire again. The repetition and statistical popping phenomena result in most of the electrical energy of the muscle signal being concentrated in the range of 200 to 600 Hz in frequency. Components of the muscle signal exist outside this frequency range, but are not as strong.

The signal from differential instrumentation amplifier DA is applied to band-pass filter BPF. The transfer function of filter BPF gives maximum gain between the 3 dB frequencies of 200 Hz and 600 Hz (the band in which most of the power in the jaw muscle signal lies). The gain of the filter at the 3 dB frequencies is down to 0.707 times its peak gain, and the gain falls off rapidly outside these frequencies. Filter BPF also provides a deep, narrow rejection notch at 60 Hz, to facilitate immunity to electromagnetic interference from household appliances and electrical utility wiring. The notch feature of the filter gives much better performance than a band-pass filter without a notch. A preferred embodiment uses a notch filter with a Q greater than 10. An ordinary forth order band-pass filter with a lower 3 dB frequency of 200 Hz would provide attenuation of 3.3 (about 10 dB) at 60 Hz. Including the notch function, an attenuation of more than a factor of 30 (about 30 dB) can be achieved.

The signal from the output of filter BPF is applied to the input of muscle threshold detector MD. This is the first non-linear element in the signal processing chain. In FIG. 6B, the signal processing block SP of FIG. 6A has been expanded into seven functional blocks. The combined function of these blocks is to provide bio-feedback (and data output), whenever there has been at least a certain amount of bruxing muscle activity above a certain threshold within a certain period of time.

Figure 6D:
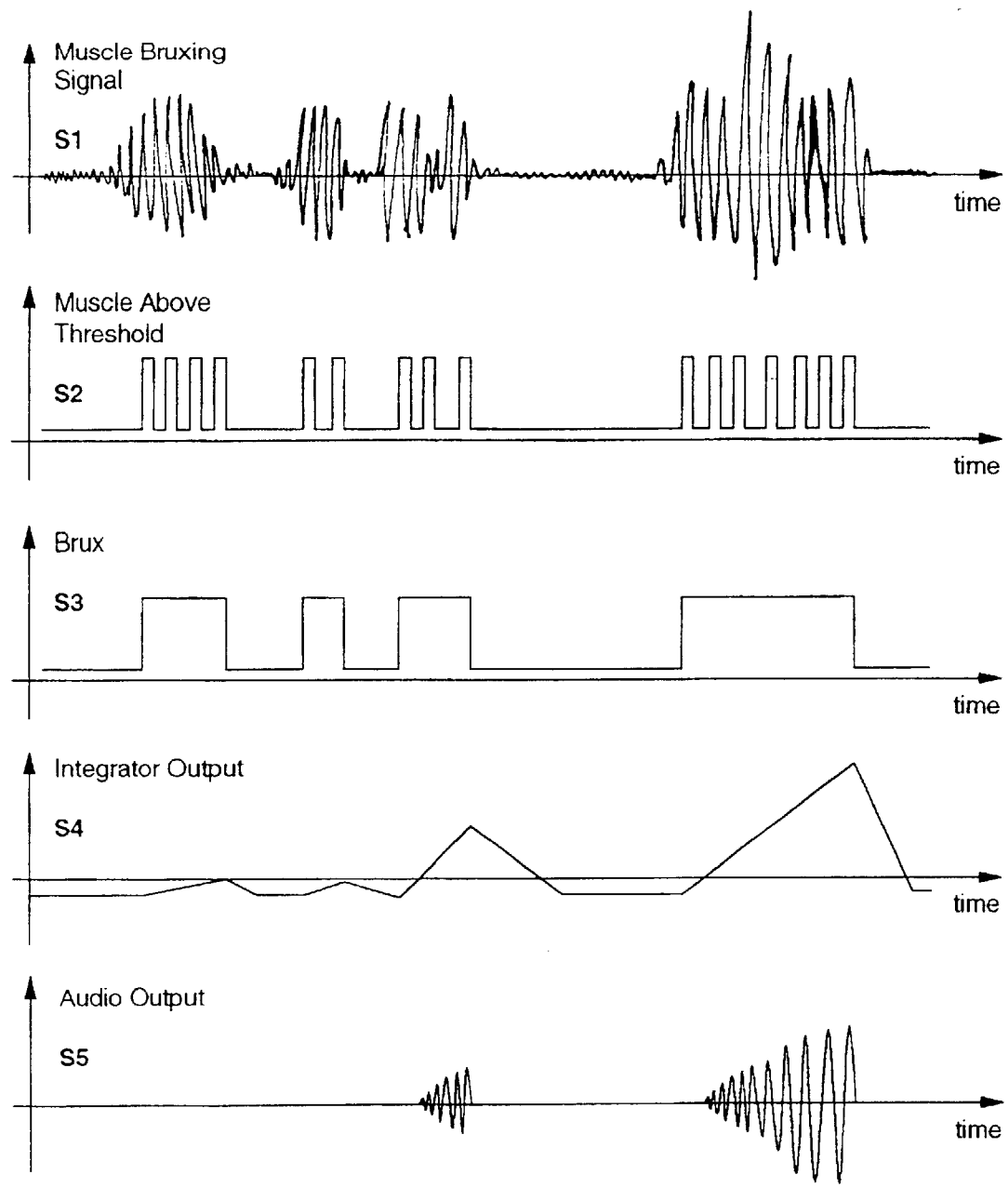
FIG. 6D shows various signals pertinent to the invention, with respect to time.

Examples of signals that will "set off" the signal processing arrangement of FIG. 6B are shown in FIG. 6D.

FIG. 6D shows exemplary waveforms showing the timing and amplitude relationship between signals S1, S2, S3, S4, and S5, as identified in the block diagram in FIG. 6B. Detector MD serves to detect when muscle signals of sufficient intensity to warrant further analysis are present. The output of muscle threshold detector MD, denoted S2, may be considered to be a digital signal, with two possible instantaneous values (0 and 1). S2 is zero all the time if the muscle signal being measured is very small, and is 1 a higher percentage of the time as the muscle signal gets stronger. The percentage of time that S2 is 1 approaches 50% as the muscle signal gets very strong. Signal S2 can be thought of as an AC signal with a variable DC bias riding on it. For strong muscle signals, the DC bias approaches half the peak value of S2. The AC portion of S2 always has its fundamental energy between 200 Hz and 600 Hz. For low muscle signals, S2 is "peaky" and has a lot of energy at higher harmonics. For higher muscle signals, where S2 is one almost half the time, S2 has most of its fundamental energy within the 200 to 600 Hz frequency band, and has the relative harmonic content of a square wave. Because the input signal to muscle threshold detector MD is a band-passed signal with most of it's power between 200 Hz and 600 Hz, the average pulse length at the output of detector MD will be about 1.2 milliseconds. The threshold of muscle threshold detector MD is adjustable to allow the user to determine what level of bruxing should be detected.

Low-pass filter LPF averages the output of muscle threshold detector MD over a period of time which is long compared to the average 1.2 millisecond pulse length of the output of muscle threshold detector MD, but short compared to human reaction time (about 0.1 sec). The output of filter LPF may be thought of as an analog voltage which is representative of the intensity envelope of the muscle signal being measured between electrodes E1 and E3. When this envelope exceeds a predetermined value, event detector ED indicates (via signal S3) that there has been enough bruxing activity "recently" to count as a bruxing event (a situation where there has been enough muscle activity at a sufficient intensity to indicate at least a brief clenching of teeth).

Event detector ED is a threshold detector which serves to detect when the muscle activity envelope has exceeded the allowable limit. When this limit is exceeded, audio oscillator AO is turned on, and the user will be able to hear a faint tone from audio transducer SK (which may be, for instance, an earphone or a piezo electric transducer held in a headband to the user's forehead). The output of limiting integrator LI begins to ramp up as soon as the output of event detector ED becomes active. As S4 (the output of integrator LI) ramps up, the gain of variable gain amplifier VGA increases proportionally, and the tone heard in audio transducer SK increases in volume. When the limit of limiting integrator LI is reached, the output volume of audio transducer SK remains at a maximum. The ramping rate of integrator LI is adjustable. Adjusting to a slower ramp rate allows the user to stop bruxing without being awakened if the device is being used at night (the user will respond by ceasing bruxing activity before the tone gets loud enough to awaken the user). As can be seen in signal S4 in FIG. 6D, the output of the limiting integrator in this embodiment is initially negative. The time taken for the S4 to ramp from its initial negative value to zero serves as a "minimum bruxing duration" delay. This delay may be used to prevent triggering on short isolated bruxing events, if desired. Repetitive bruxing bursts will allow the integrator to ramp up beyond zero, if they are closely spaced in time. Thus, repetitive clicking of teeth (a common form of nocturnal bruxism) will result in biofeedback. The aim here is to provide biofeedback for the majority of events that can lead to cumulative damage to teeth, while not responding to events that could come from something like a person moving to a new sleep position.

Enabling audio oscillator AO from S3 (the output of event detector ED) provides the additional feature that if the person stops bruxing in response to the tone heard through the audio transducer, the tone stops immediately, rather than ramping back down slowly with the output of limiting integrator LI.

Power is supplied to the unit by battery stack B (4 lithium coin cells), through power switch SW.

OTHER EMBODIMENTS

Figure 5A:
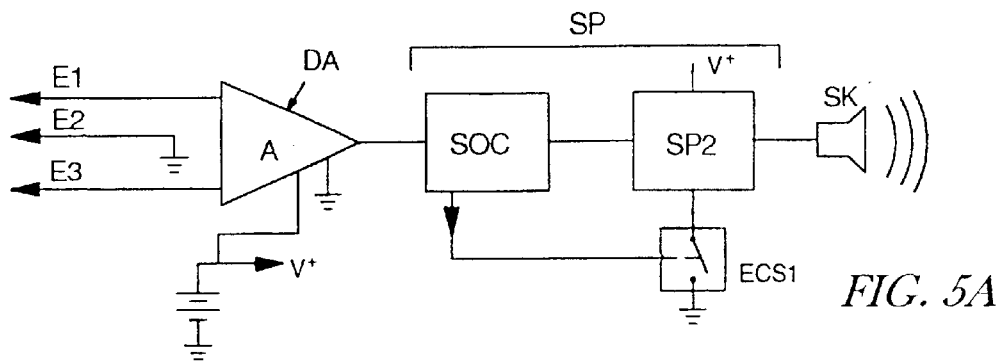
FIG. 5A is a schematic block diagram depicting an embodiment where operating-condition-sensing circuitry SOC senses a condition at electrodes E2 and E3 (through differential amplifier DA) which indicates whether the unit is connected to the user.
Figure 5B:
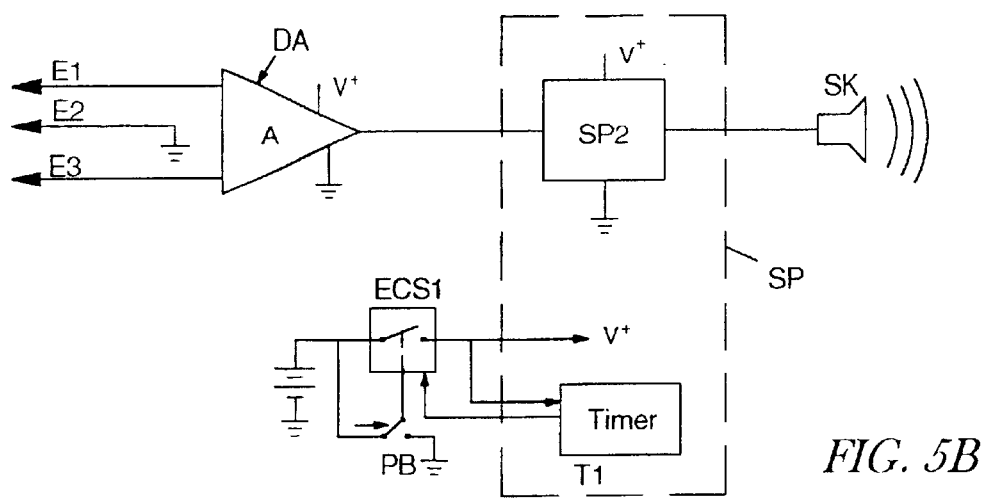
FIG. 5B is a schematic block diagram depicting an embodiment where the power to both Differential Amplifier DA and signal Processing circuitry SP2 are controlled by electronic Switch ECS1, where electronic switch ECS1 may be turned on and off by Push-button Switch PB, or may be turned on by PB, and turned off a fixed amount of time later by Timer T1.

Other embodiments of the invention than the one shown schematically in FIG. 6B are contemplated. The signal processing block SP may include numerous timing and auxiliary functions, as illustrated in FIGS. 5A–5D. For instance, as shown in FIG. 5B the power switch SW may be modified to be an electronically controlled switch ECS1, allowing part of the circuitry (for instance, the bio-feedback and data logging) to be switched while the front end amplifier is designed for extreme low power consumption and may remain continuously active. This feature combined with the addition of circuitry SOC for sensing proper operating conditions, allows for an automatic on/off function. (The remainder of signal processing block SP in this implementation is shown as block SP2.) One possible implementation of such a function assumes that amplifier/filter AF is designed such that if the unit is removed or improperly worn, the output from amplifier/filter AF goes out of range. When proper operating conditions are present (electrodes making good contact with skin, no bruxing event currently being detected), the output of amplifier/filter AF is in range. The front end of signal processing block SP (detector SOC) may be implemented with the ability to detect this condition and shut down the unit. The unit may be shut down immediately or after several seconds of alarm, alerting the user to correct the problem if it is not intentional. The electronics may be designed to overload on 60 Hz and provide a continuous brux indication when removed from the head, so that the prolonged brux signal may be used to implement an automatic shut-off feature. In another embodiment, shown schematically in FIG. 5B, electronically-controlled switch ECS1 may be activated in aresponse to a momentary push-button switch PB, and deactivated in response to timer T1, allowing the user to turn the unit on for a predetermined period of time (for instance by a momentary push-button). This feature may be combined with the automatic-off function described above, for convenience and minimal power consumption. In such an embodiment, the user turns the unit on with a push-button, and the unit turns itself off a set time after having been removed. This embodiment and others may incorporate means allowing for the automatic disabling of the bio-feedback means for a fixed time after the unit is turned on (to allow the electrodes to "sweat in" and become reliable contacts).

Figure 5C:
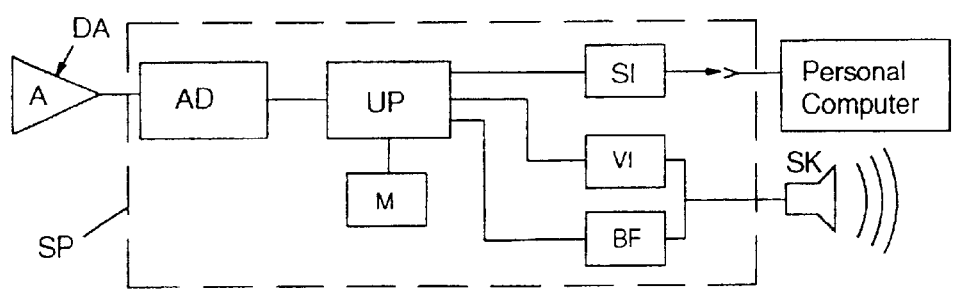
FIG. 5C is a schematic block diagram depicting an embodiment detailing a possible embodiment of Signal Processing block SP, including an analog-to-digital converter and a microprocessor UP and a memory M.
Figure 5D:
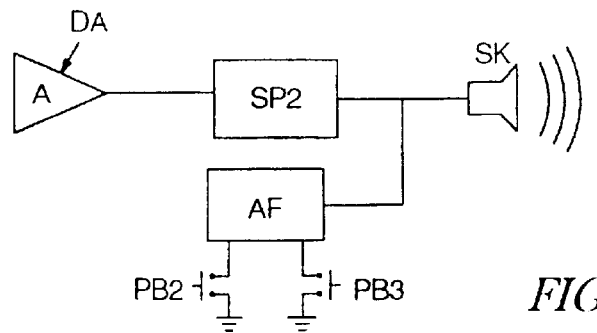
FIG. 5D is a schematic block diagram depicting an embodiment where time keeping and alarm means ALM have been added to provide an alarm-clock-type function.

In another embodiment, shown schematically in FIG. 5C, signal-processing means SP may include an analog/digital interface AD, a microprocessor UP and memory M, allowing the digital storage and retrieval of bruxing event data, including event timing, duration, and intensity data. Retrieval may be accomplished by connecting a personal computer or the like to an RS232 interface SI (implemented on many single-chip microprocessors). For ease of interfacing to the user, data retrieval may also be accomplished by a microprocessor-driven Voice interface VI, using a voice synthesis chip such as are used to time-stamp messages on telephone answering machines. Voice interface VI and bio-feedback means BF may interface to the user through the same audio transducer SK. In addition, the character of the bio-feedback signal provided may be varied over time, to prevent the user getting "used to it" and "tuning it out". For instance, in an embodiment using audio bio-feedback, the sound could be a tone one time, a barking dog the next, and a meowing cat the next.

Further features may be added, giving additional functionality and value to the consumer. In one embodiment, shown schematically in FIG. 5D, an "alarm clock" function may be added, utilizing time keeping and alarm means AF, that can either wake up the user at a specific time of day (via the bio-feedback means), or after a pre-determined time (to allow, for instance, for 8 hours of sleep). Time keeping and alarm means AF may be set via push-buttons PB2 and PB3, and may sound the alarm through audio bio-feedback means SK.

SCHEMATIC

FIG. 7 is a schematic circuit diagram of a preferred embodiment of the invention shown in block diagram form in FIGS. 6A–6C. Other circuit implementations would be evident to one of ordinary skill in the art, and the embodiment shown in FIG. 7 is not intended to be limiting in any way. Wires from the electrodes come in through a housing H via connector J1. Resistors R38 and R39 provide current limiting to prevent damage from static discharge. Amplifiers U1A and U1D, together with R35, R36, R37, and C13 comprise a high-input-impedance differential input amplifier DA. Capacitor C36, in conjunction with resistor R36 lowers the DC gain of the differential input amplifier to unity, while the in-band gain is 10. This allows immunity to chemical offset voltages at the electrodes.

Amplifier U1C, in conjunction with resistors R1, R32, R2, and R31, and capacitors C12 and C14 comprise a differential-to-single-ended converter, which together with the input differential amplifier constitutes differential instrumentation amplifier DA.

Amplifiers U2A, U2B, U2C, and U2D, in conjunction with resistors R21, R22, R23, R24, R26, R27, R28, R29, R30, R33, R34, R3, and capacitors C1, C2, C8, and C9 comprise band pass filter B/F, with a pass band between 200 and 600 Hz, and a rejection notch at 60 Hz. Potentiometer R3 may be used to precisely tune the 60 Hz rejection notch.

Capacitors C17, C16, C7, and C11 provide bypassing of the power supply rails, which are derived from battery stack B through connector J3.

Amplifier U2B, in conjunction with potentiometer R4 and resistor R16 comprise variable threshold detector MD.

Resistor R25 and capacitor C10 constitute low-pass filter LPF.

Amplifier U3A, in conjunction with resistors R5, R18, and R19 constitute threshold detector ED.

Transistor Q2, in conjunction with resistors R9, R20, and diode D1A, provide buffered data output DO1. The signal buffering provided by Q2 prevents attached data-logging equipment from affecting the operation of limiting integrator LI.

Amplifier U3C, in conjunction with resistors R6, R10, R12, R13, capacitor C6, and diode DIB constitute gated audio oscillator AO.

Amplifier U3D, in conjunction with Capacitor C3 and resistor R17 constitute limiting integrator LI.

Transistor Q1, in conjunction with resistors R7, R8, and R14, capacitors C4 and C5, and amplifier U3B constitute variabl-egain amplifier VGA.

Transistor Q3, in conjunction with resistors R11 and R15, and diode D2B, provide buffered data output DO2. Capacitor C1S rovides coupling for audio output AO1. Data outputs DO1 and DO2, and Audio output AO1 are available through connector J4. Piezo audio is available through connector J2.

FIGS. 9A, Part 1, 9A Part 2 and 9A Part 3 and 9B, Part 1, 9B Part 2, 9B Part 3 and 9B Part 4 show detailed circuit diagrams of a preferred embodiment of the invention. A microprocessor, digital display, and two switches allow setting of sensitivity, alarm volume, and on/off functions. Cumulative data on the number of bruxing or clenching events and the total duration of bruxing and clenching can be displayed. In this embodiment, the microprocessor automatically shuts off power to the analog circuitry and goes into a super-low power sleep state after seeing an above-trigger-level signal for more than 30 seconds.

SOME IMPORTANT FEATURES

Some important features of the invention include:

Non-adhesive pressure-contacting electrodes;

Wearable bruxing detector;

Data-logging (event count, duration info, time of incident info);

Can be neck band;

Some embodiments use temporalis-only detection;

Can be head band;

Can be "C" band (like headphones);

Pickup electrodes can be Ear clips;

Pickup electrodes can be ear inserts;

Pickup electrodes can be earrings;

Pickup electrodes can be glasses frame;

Integration following threshold detector to generate alarm (not novel except in combination with other features);

Hydraulically impermeable electrode surfaces;

Alarm intensity ramp;

Delayed start after power-up (Settle-in timer);

Front end powered all the time that powers up rest of unit if in linear range for a given time;

Auto-shut-off after predetermined time;

Wake-up alarm;

Combination with transmitted data logging (ultrasonic or IR or Radio);

Back of audio actuator (for example, the cover of a piezo electric transducer) may be a conductive surface which doubles as ground reference electrode;

Coupling audio signal mechanically to the bones of the user's head is highly efficient and gets sound to both ears, while still being much quieter to person sleeping next to user;

Early removal alarm;

Separable cloth and electrodes;

Headband can use rubber loop electrodes;

Internal RAM and UART;

Data logging of intensity logging of number of events logging of timing of events.

Flex-circuit sewn inside fabric headband for comfort and aesthetics;

Conductive rubber electrodes sewn on or conductive rubber applied directly to areas of fabric;

Thin conductive-rubber-coated-fabric patches may be sewn on as electrodes, and folded under at the edges for attachment to flex-circuit by rivets (which get automatically covered by the folded over fabric).

The foregoing discussion should be understood as illustrative and should not be considered to be limiting in any sense. While this invention has been particularly shown and described with references to preferred embodiments thereof, it will be understood by those skilled in the art that various changes in form and details may be made therein without departing from the spirit and scope of the invention as defined by the claims.

Having described the invention, what is claimed is:

1. An apparatus for sensing the occurrence of bruxism by a human user and signaling said user by acoustically coupling to said user's head, said apparatus comprising:
   a. a plurality of electrically conductive electrodes;
   b. means for pressing said plurality of electrodes against the external body skin of said user by positive pressure at a location on said user's body where said electrodes receive low-voltage muscle signals generated by bruxism muscles of said user that are active during the occurrence of bruxism;
   c. sense/amplification means for sensing the differential voltage between at least two of said electrodes and selectively amplifying the electrical signals generated by bruxism muscles, such signals termed "bruxism activity signals";
   d. a detector that generates a bruxism event signal when said bruxism activity signal satisfies pre-determined time and amplitude conditions; and
   e. acoustical output means for mechanically coupling an audio-band vibrational output signal that corresponds to said bruxism event signal to said user's head.

2. The apparatus of claim 1, wherein said acoustical output means comprises a piezoelectric transducer.

3. The apparatus of claim 1, wherein said plurality of electrodes comprises one reference electrode and two measurement electrodes.

4. The apparatus of claim 3, wherein said acoustical output means comprises a piezoelectric transducer.

5. The apparatus of claim 4, wherein one electrode of said piezoelectric transducer comprises said reference electrode.

6. The apparatus of claim 1, wherein at least one of said electrically conductive electrodes comprises a substantially flat conductive rubber pad attached to a substantially flexible band disposed circumferentially around the users head.

7. The apparatus of claim 5, wherein at least one of said electrically conductive electrodes comprises a substantially flat conductive rubber pad attached to a substantially flexible band disposed circumferentially around the user's head.

8. A method for treatment of bruxism through acoustical bio-feedback mechanically coupled to the head of a human user, said method comprising:
   a. picking up surface EMG signals from bruxing muscles through electrodes held in contact with the skin near said bruxing muscles;
   b. selectively amplifying said EMG signals in a frequency band where said signals are strongest, while substantially attenuating 60 Hz signals in comparison to said selective amplification;
   c. subjecting said amplified signals to decision-making criteria based on time and amplitude, to distinguish events defined by said criteria as "bruxing events";
   d. mechanically coupling, at a first output level of intensity, an audio-band acoustical bio-feedback signal to the head of said user in response to said bruxing events.

9. The method of claim 8 wherein said first output level of intensity is a low output level of intensity, further comprising:
   a. increasing said output level of intensity of said bio-feedback signal over time until either a maximum is reached, or cessation of bruxing is detected; and
   b. rapidly terminating said bio-feedback signal in response to cessation of said bruxing signal.

* * * * *